US012589253B2

(12) United States Patent
Sama et al.

(10) Patent No.: US 12,589,253 B2
(45) Date of Patent: Mar. 31, 2026

(54) SYSTEM AND METHOD FOR ALIGNING A CHARGER FOR AN IMPLANTED MEDICAL DEVICE

(71) Applicant: Axonics, Inc., Irvine, CA (US)

(72) Inventors: Rinda Sama, Irvine, CA (US); Faizal Abdeen, Mission Viejo, CA (US)

(73) Assignee: Axonics, Inc., Irvine, CA (US)

( * ) Notice: Subject to any disclaimer, the term of this patent is extended or adjusted under 35 U.S.C. 154(b) by 347 days.

(21) Appl. No.: 18/196,386

(22) Filed: May 11, 2023

(65) Prior Publication Data

US 2023/0364436 A1      Nov. 16, 2023

Related U.S. Application Data

(60) Provisional application No. 63/340,827, filed on May 11, 2022.

(51) Int. Cl.
*A61N 1/378*          (2006.01)
*A61N 1/372*          (2006.01)

(52) U.S. Cl.
CPC ....... *A61N 1/3787* (2013.01); *A61N 1/37229* (2013.01); *A61N 1/37282* (2013.01)

(58) Field of Classification Search
CPC .............. A61N 1/3787; A61N 1/37229; A61N 1/37282
USPC ........................................................ 607/61
See application file for complete search history.

(56) References Cited

U.S. PATENT DOCUMENTS

| | | | |
|---|---|---|---|
| 9,339,660 B2 * | 5/2016 | Feldman | .............. A61N 1/3787 |
| 2017/0143981 A1 | 5/2017 | Aghassian | |
| 2022/0016430 A1 | 1/2022 | Hartley et al. | |

OTHER PUBLICATIONS

International Search Report and Written Opinion mailed Aug. 11, 2023 issued by the International Searching Authority in related International Application No. PCT/US2023/021766; filed May 10, 2023.

* cited by examiner

*Primary Examiner* — Nadia A Mahmood

(74) *Attorney, Agent, or Firm* — Seager Tufte & Wickhem, LLP

(57)          ABSTRACT
Devices, systems and methods for improving alignment of a charging device with an implanted medical device are disclosed herein. The system can include an external charging device that communicates one or more charge parameters during charging to a user device having an alignment feature that is embodied in a software application that displays a real-time charging efficiency indicator based on the charge parameters. This alignment feature allows determination of an optimal position by observing charging efficiency while moving the charging device during charging. The application and device may be configured for use by a specialist, such as a field technician or representative of the device provider, to aid the patient. The system can further include a charging device configured for use with the application and having additional charging functionality. The alignment feature may be included for training and/or troubleshooting charging alignment problems experienced by certain patients.

32 Claims, 31 Drawing Sheets

1300

1400

1401

1500

1501

1600

1601

1700

1701

1800

1801

Fine-Tune Alignment

-Charging in Process

-GUIDANCE:
   Move Charger Up Slowly Until
Continuous Beep Indicates
Alignment

2200

AXONICS

*SmartCHARGE*

CONNECT TO CHARGER

1. ENSURE THIS DEVICE HAS BLUETOOTH ON.
2. TURN ON THE CHARGER.
3. ENTER THE 10-DIGIT SERIAL NUMBER ON THE BACK OF THE CHARGER.

CONNECT

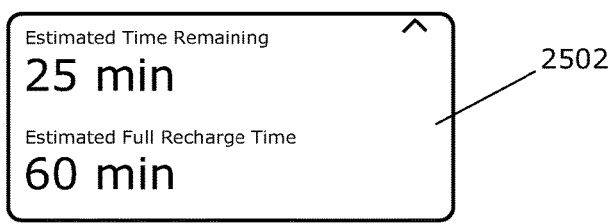
Estimated Time Remaining
25 min
Estimated Full Recharge Time
60 min
2502
FIG. 25
| Levels | Percentage |
|--------|------------|
| 1 | 0-20 |
| 2 | 20-40 |
| 3 | 40-60 |
| 4 | 60-80 |
| 5 | 80-100 |
2601
FIG. 26
| Levels | Aligned at (Degree) |
|--------|---------------------|
| 3 | 60 |
| 4 | 30 |
| 5 | 0 |
2701
FIG. 27
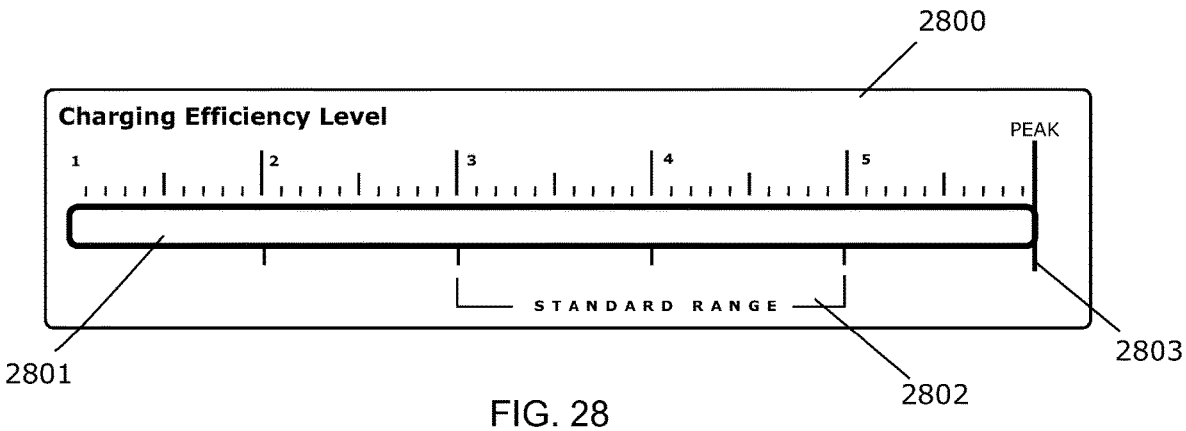
2800
Charging Efficiency Level
1    2    3    4    5    PEAK
STANDARD RANGE
2801
2802
2803
FIG. 28

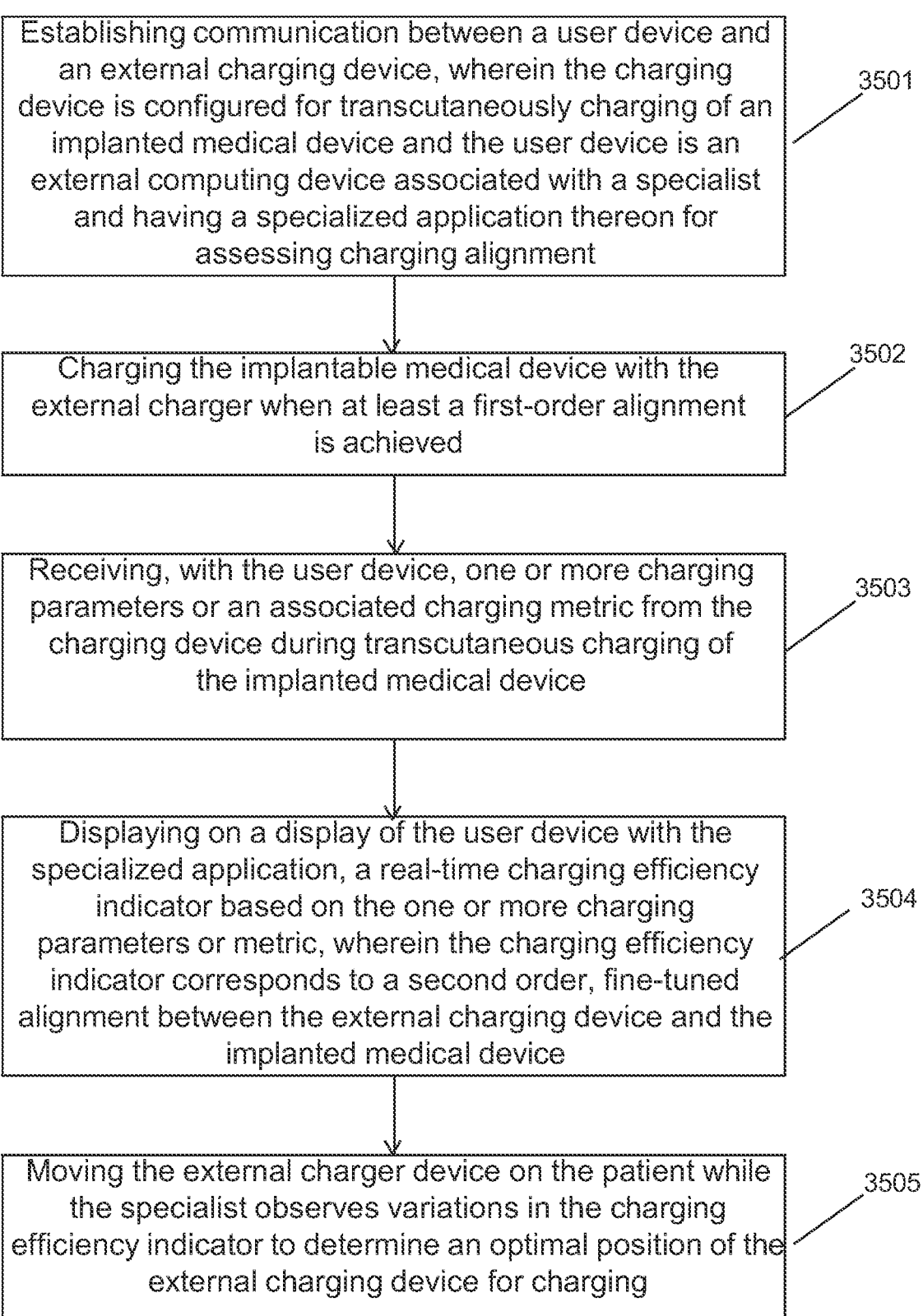

Establishing communication between a user device and an external charging device, wherein the charging device is configured for transcutaneously charging of an implanted medical device and the user device is an external computing device associated with a specialist and having a specialized application thereon for assessing charging alignment — 3501

Charging the implantable medical device with the external charger when at least a first-order alignment is achieved — 3502

Receiving, with the user device, one or more charging parameters or an associated charging metric from the charging device during transcutaneous charging of the implanted medical device — 3503

Displaying on a display of the user device with the specialized application, a real-time charging efficiency indicator based on the one or more charging parameters or metric, wherein the charging efficiency indicator corresponds to a second order, fine-tuned alignment between the external charging device and the implanted medical device — 3504

Moving the external charger device on the patient while the specialist observes variations in the charging efficiency indicator to determine an optimal position of the external charging device for charging — 3505

FIG. 35

SYSTEM AND METHOD FOR ALIGNING A CHARGER FOR AN IMPLANTED MEDICAL DEVICE

CROSS-REFERENCES TO RELATED APPLICATIONS

This application claims priority to U.S. Provisional Application No. 63/340,827, entitled "Implanted Medical Device Charger Alignment Tools and Methods for Use, Training, and Trouble Shooting," filed on May 11, 2022, which is incorporated herein by reference in its entirety for all purposes.

The present application is also generally related to U.S. Non-Provisional application Ser. No. 17/522,644, entitled "Devices and Methods for Fine-Tuning Alignment of Charging Device with Implanted Medical Device," filed on Nov. 9, 2021, which is assigned to the same assignee and incorporated herein by reference in its entirety for all purposes.

BACKGROUND

The present application relates to implantable neurostimulation treatment systems and associated charging devices and methods.

The prevalence of use of medical devices in treating ailments is increasing with time. In many instances, and as these medical devices are made smaller, these medical devices are frequently implanted within a patient. To power such devices, external charging devices that transcutaneously transfer energy to the implanted device are used to power the implanted device or to recharge a rechargeable battery of the implanted device. Such external charging devices typically utilize a charging coil that inductively couples with an internal coil of the implanted medical device. Efficient transcutaneous transfer of energy requires that the coils be suitably aligned. Misalignment can result in failure to recharge, inefficient recharging and/or excessive heat generation. While some conventional systems include features to indicate alignment, these features typically indicate merely when alignment is suitable for charging to take place within acceptable limits and typically do not facilitate precision placement to ensure optimal charging occurs. This can result in sub-optimal alignment that leads to prolonged recharging times and/or excessive heat generation. Further, current approaches of indicating alignment typically lack detailed guidance to facilitate the patient or clinician in providing precision alignment.

Therefore, there exists a need for devices, systems and methods that facilitate improved, precision alignment between an external charging device and an implanted medical device. There is further need for an approach that provides guidance on improving alignment in a manner that is intuitive, interactive and utilizes features of existing systems.

SUMMARY

In one aspect, the subject matter pertains to charging of an implantable pulse generator by an external charging device, and particularly, devices and methods for improving alignment between charging coils of an implanted medical device and an external charging device.

In some embodiments, the system is configured such that a device determines an alignment indicator based on charging efficiency determined from one or more charging parameters. The alignment indicator may be an output of the real-time charging efficiency during charging. The system outputs the indicator, which corresponds to alignment, during charging. Typically, the indicator indicates alignment without modifying the charging operation based on the alignment determination. This indicator facilitates a precision adjustment of alignment, either by the patient or clinician, during the charging operation. In one aspect, the alignment feature described herein may be incorporated into a user device of a specialist (e.g., field technician associated with the device manufacturer, clinical care specialist) to allow the specialist to assist the physician and/or patient in positioning the device. Such a feature is particularly advantageous for training after initial implantation and for troubleshooting alignment problems experienced by some patients. In some embodiments, the alignment feature may be embodied in a software application accessible/authorized for use only by the specialist, not by the patient, the treating physician or clinician device. In some embodiments, the alignment tools include a user device having the specialized software application thereon and configured for use with a standard charging device or a specialized charging device with added functionality. These aspects may be applied to any of the embodiments described herein.

In some embodiments, the system includes a first indicator that indicates a first-order alignment (rough alignment) that corresponds to when alignment between coils is sufficient to inductively transfer energy for transcutaneously charging, and a second indicator that indicates a second-order alignment (precision alignment) within a range of suitable alignment positions to facilitate fine-tuned adjustment of alignment to increase charging efficiency and reduce charging time. In some embodiments, the system can include a third indicator that indicates when the optimal alignment position is reached. The first, second and third indicators are distinct from each other so that a user and/or clinician can readily distinguish between each indicator.

Alignment between the charging device and the implanted device may be considered to be of a first order or a second order. In some embodiments, the charging device includes certain indicators for indicating a first order alignment (i.e., rough alignment) so that the user can determine whether initial placement is suitable to establish inductive coupling and commence charging, and certain other alignment indicators are used to indicate a precision or second order alignment (e.g., fine-tined alignment during charging to improve or optimize charging). Typically, loss of first order alignment loses inductive coupling, which stops charging completely, whereas losing precision or second order alignment reduces charging efficiency/optimization during charging. In some embodiments, the certain other alignment indicators are indicators provided by the charging device that are readily distinguishable from the first order indicators. In some embodiments, the certain other alignment indicators are provided by an external user device (e.g., smartphone, tablet) of the patient or clinician. The certain other alignment indicators may be determined and output by a specialized software application on a standard user device specific for improving alignment of the charging device. In some embodiments, the certain other indicators for second-order alignment are only provided by the user device. In some embodiments, the charging device includes the first-order alignment indicators, while the user device includes indicators for both first-order alignment and second-order alignment.

In some embodiments, the alignment indicator is determined during standard charging operation and output to a user (e.g., specialist, patient and/or clinician) in real-time during charging to allow the user to dynamically adjust the alignment of the charging device based on the indicator. In some embodiments, the alignment indicator is a charging efficiency indicator from which the user can ascertain optimal alignment. The indicator may be incorporated into the charging device or may be provided by a user interface of one or more external devices. The indicator can include, but is not limited to, any of or any combination of visual, audio, and haptics. In some embodiments, the indicator may be provided on or across multiple devices, for example, the indicator may be provided on both a clinician and patient device, for example, a first indicator may be provided by the charging device and the second and/or third indicator may be provided on one or more external computing devices of the patient or clinician. This allows additional functionality regarding precision placement to complement existing charging devices already having minimal alignment features.

In some embodiments, the external charging device includes a power button and one or more visual indicators, such as but not limited to one or more light indicators (e.g., flashing, on, off) and one or more audio indicators (e.g., one or more tones/beeps). The light indicators may be used to indicate any of, but not limited to, a power state (e.g., green on), a battery state of the external device (e.g., orange on), orange flashing), error states (e.g., red), and charging status (e.g., flashing green). In some embodiments, the charging device charges the implanted medical device in a closed-loop charging state during standard charging and an open-loop loop charging state if the implanted medical device battery is too low to perform closed loop charging and can optionally include various other charging states (e.g., slow charge, fast charge, etc.). In some embodiments, any indicator of the charging device that indicates charging does not identify or distinguish between the differing charge states. The audio indicators may be used to indicate any of initial alignment suitable that commences charging (e.g., long tone), completion of charging (e.g., three rising tones), and error states. In some embodiments, the external charging device includes a haptic indicator for indicating a change in charge status necessitating user intervention (e.g., first order misalignment, loss of charge coupling). This is particularly advantageous when the implanted medical device is implanted in the lower back/upper buttock region where the patient cannot view visual indicators on the charging device. This implantation region is common in sacral neuromodulation systems for treatment of urinary and/or fecal incontinence. The use of a haptic feature for loss of alignment/charging facilitates an immediate patient response to correct/re-align the charging device to restore charging. Notably, conventional devices typically rely on an assortment of audio and visual indicators (e.g., various patterns of beeps and flashing lights), which may be more easily disregarded or confused by the patient, and thus may cause undue delay in restoring charging. When first order alignment is unsuitable, charging stops completely, such that the implanted medical device may not be able to be charged within the time available to the patient or greatly prolonging the charging session. Therefore, it is advantageous for this event to be indicated by a unique indicator (e.g. haptic vibration) that is instantly recognizable by the patient and easily distinguished from the assorted beeps/flashing lights commonly used for various other charging events (e.g. starting, charging status, battery, completion, etc.). In some embodiments, the charging device includes a haptic indicator only for loss of charging due to misalignment in first-order alignment.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 25-28 show exemplary battery and charge information indicators, in accordance with some embodiments.

FIG. 35 shows an exemplary method of optimizing charging device alignment by a specialist using a specialized software application, in accordance with some embodiments.

DETAILED DESCRIPTION

Figure 1:
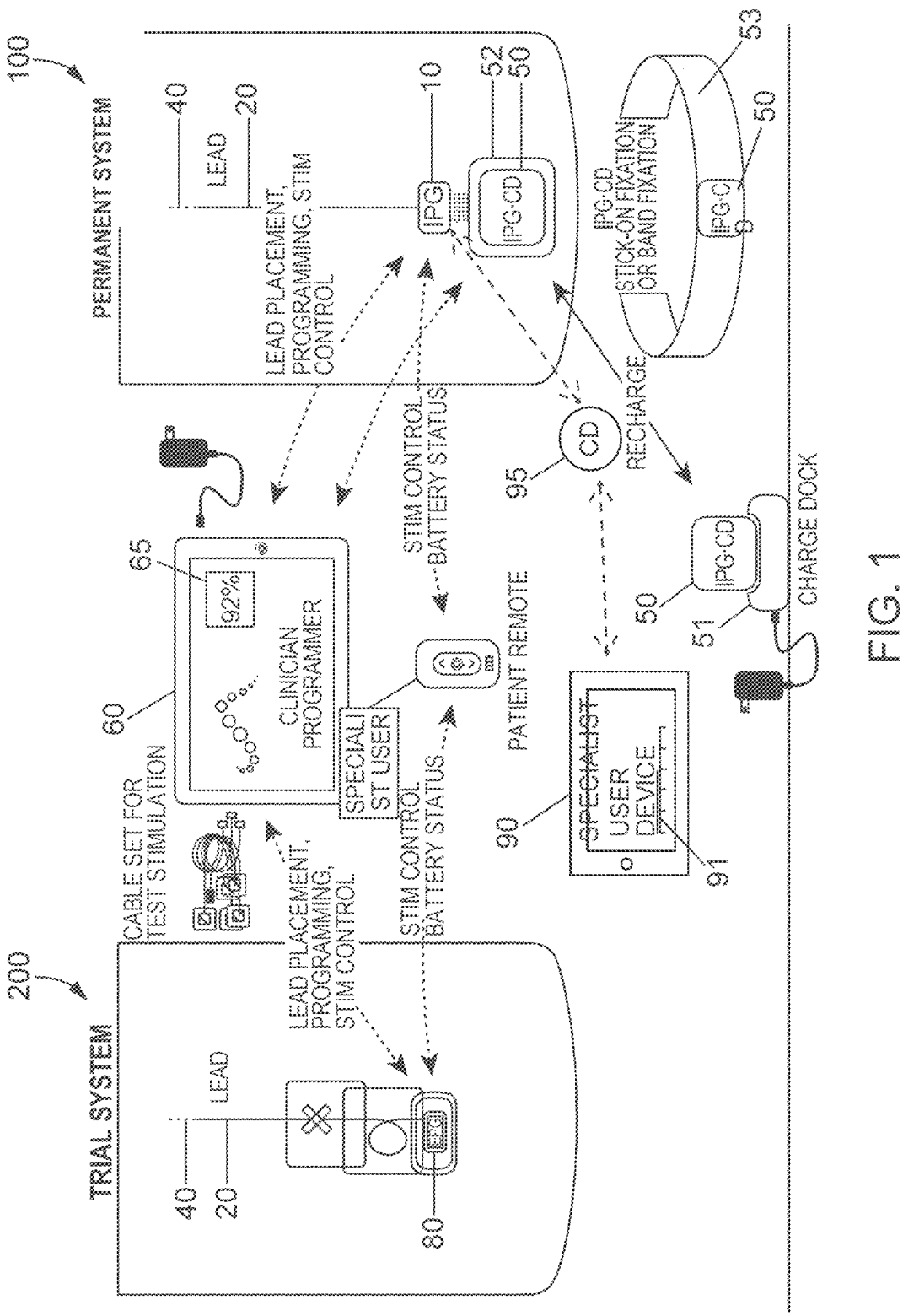
FIG. 1 schematically illustrates a nerve stimulation system, which includes a clinician programmer of both a trial neurostimulation system and a permanently implanted neurostimulation system, in accordance with some embodiments.

The subject matter relates to recharging of implanted medical devices, in particular, neurostimulation treatment systems and associated devices. In some embodiments, the subject matter relates to charging of an implanted neurostimulator of sacral nerve stimulation treatment systems configured to treat overactive bladder ("OAB") and relieve symptoms of bladder related dysfunction. It will be appreciated, however, that the subject matter may also be utilized for any variety of neuromodulation uses, such as fecal dysfunction, the treatment of pain or other indications, such as movement or affective disorders, as well as various other implantable medical devices as understood by one of skill in the art.

In some embodiments, the subject matter pertains to a device that obtains one or more charging parameters from the charging device and/or the implantable neurostimulator and outputs an alignment indicator based on the one or more charging parameters that is indicative of precision alignment between the charging device and implanted device. Currently, many implantable neurostimulation system include a receiving coil that receives energy transcutaneously from a charging coil in an external charging device placed on the patient's skin over the charging device. Exemplary charging device are described in U.S. application Ser. No. 16/816, 006, and U.S. Pat. No. 10,682,521, the entireties of which are incorporated herein by reference or all purposes. The precise alignment between the charging coil and the receiving alignment, including alignment along x and y axes along the patient's skin, as well as rotational orientation, largely determines the efficiency of charging. Typically, conventional systems provide charging so long as the charging device is within the range of suitable positions, however, many positions within this range may provide suboptimal charging at reduced charging efficiency, which can lead to patient discomfort and poor charging, as described above. Thus, various embodiments allow for precision placement of the charging device to fine-tune alignment between the coils of the charging device and the implanted neurostimulator. It is appreciated that although the concepts herein are described regarding a particular type of neurostimulation system, the concepts described herein are applicable to any type of neurostimulation system and further applicable to any charging device for an implanted medical device that would benefit from optimal alignment and placement on the patient.

I. Neurostimulation Indications

Neurostimulation (or neuromodulation as may be used interchangeably hereunder) treatment systems, such as any of those described herein, may be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments may be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

II. Sacral Neuromodulation

Sacral Neuromodulation (SNM) is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, are supported by multiple studies and are well-documented. SNM has also been approved to treat chronic fecal incontinence in patients who have failed or are not candidates for more conservative treatments.

A. Implantation of Sacral Neuromodulation System

Currently, SNM qualification includes a trial phase with an external neurostimulator and is followed, if successful, by a permanent implant with a fully implantable, rechargeable neurostimulator. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding may be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The subject matter relates to a system adapted to deliver neurostimulation to targeted nerve tissues in a manner that disrupts, inhibits, or prevents neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

Figure 3:
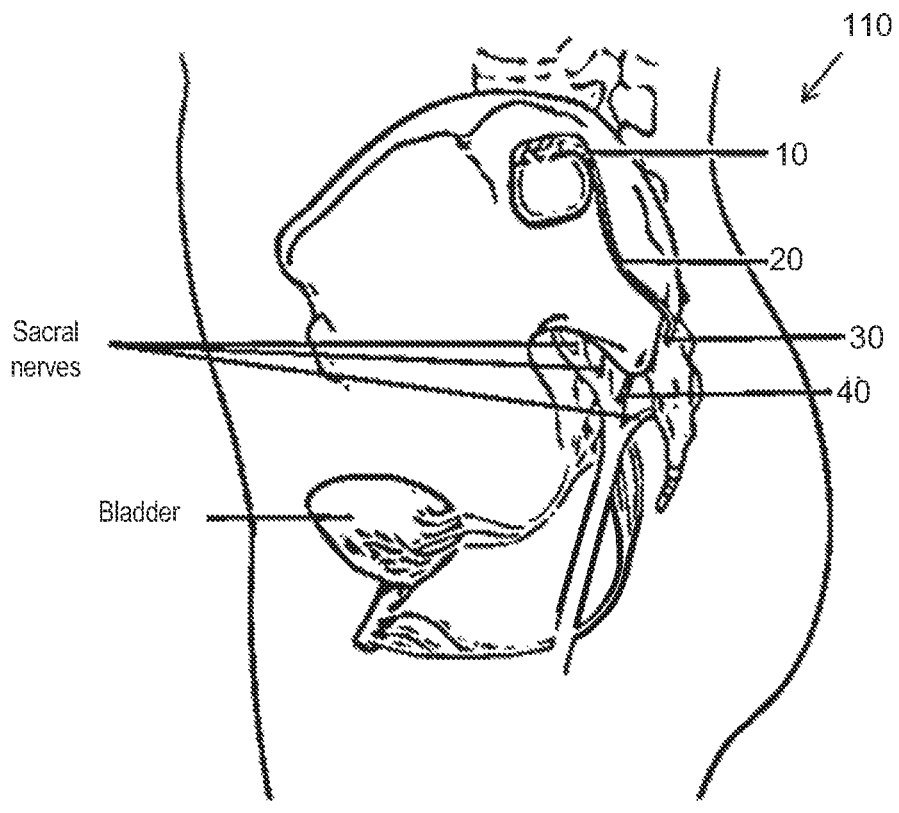
FIG. 3 shows an example of a fully implanted neurostimulation system, in accordance with some embodiments.

Sacral nerve modulation applications typically involve implantation of the implantable neurostimulation device in the lower back/upper buttock region of the patient to better access the sacral nerve through the sacrum (see FIG. 3). This placement of the external charging device may be difficult to observe for the patient, thereby frustrating precision placement, particularly over time due to migration and fluctuations in body weight. While current neurostimulation systems have provided marked improvements in efficiency of stimulation, such systems typically require periodic recharging by use of an external charging device positioned on the patient over the device. Typically, the patient recharges the neurostimulator on a periodic basis, such as every few days, weekly or monthly, depending on the frequency of use and stimulation level of therapy. If the charging device is optimally placed, many implantable neurostimulators may be recharged in less than two hours, often within an hour or less, with minimal patient discomfort. However, if not precisely placed, recharging can take notably longer, for example, well over an hour, such as three or more hours. Further, suboptimal placement can result in build-up of excessive heat and the prolonged contact of the external charging device can cause considerable annoyance and patient discomfort. Therefore, it is desirable to provide devices and methods that facilitate precision placement of the charging device with accuracy and consistency, as described further below.

B. Example Embodiments

FIG. 1 schematically illustrates an exemplary nerve stimulation system, which includes both a trial neurostimulation system 200 and a permanently implanted neurostimulation system (INS) 100. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing, or decreasing stimulation), and/or to monitor battery status with the patient remote. This approach also allows for an almost seamless transition between the trial system and the permanent system.

The electrical pulses generated by the EPG and IPG are delivered to one or more targeted nerves via one or more neurostimulation electrodes at or near a distal end of each of one or more leads. The leads can have a variety of shapes, may be a variety of sizes, and may be made from a variety of materials, which size, shape, and materials may be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and may be configured to deliver electrical pulses to the peripheral nerve such as may be used to relieve chronic pain. The leads and/or the stimulation programs may vary according to the nerves being targeted.

To further improve placement of the charging device on the patient to provide optimal, fine-tuned alignment, the system can include an alignment tool, which can include an alignment indicator on a user device or the charging device itself that allows the user to observe a real-time indicator of coil alignment during manual positioning of the charging device. In this embodiment, the alignment tool is embodied in a separate specialist user device 90 that communicates with a specialized charging device 95 for charging the INS 10, which may be used by a specialist (e.g. field technical, representative of device provider, clinical care specialist). This alignment feature is particularly applicable to a sacral neurostimulation system, such as that described, since the implantable pulse generator is implanted in the patient's lower back/upper buttock region, where it may be difficult for the patient to view placement during manual positioning of the charging device. In the embodiment in FIG. 1, the clinician programmer 60 includes alignment indicator 61 that is configured to display an alignment indicator, which may be used by the clinician to facilitate precise placement of the charging device by viewing one or more charging parameters or associated charging metric in real-time during the charging operation. Alternatively, or in addition, the alignment indicator may be provided on specialist user device 90. In this embodiment, the alignment indicator is a charging efficiency indicator 91 based on one or more parameters received from specialized charging device 95 during charging of the INS 10.

The implantable permanent system includes a charging device 50 that is configured to transcutaneously charge the implantable pulse generator by inductively coupled coils. Typically, the implantable pulse generator includes a single receiving coil and the charging device 50 includes a single transmitting coil. When the charging device 50 is placed in proximity to the implantable pulse generator, the charging device and implantable pulse generator establish communication and initiate a charging protocol. Upon initiation of an alignment procedure upon receiving a request by an external user device 60, 90, the charging device 50, 95 can output one or more charging parameters to the respective user devices or utilize an alignment module that is distinct from a charging module, to determine and output the charging parameters or an alignment metric to the external user device. The charging devices 50, 95 can also include an adhesive attachment device 52 or charging belt 53 to maintain the charging device 50 in position on the patient during charging.

The clinician programmer 60 includes a control unit which can include a microprocessor and specialized computer-code instructions for implementing methods and systems for use by a physician in deploying the treatment system and setting up treatment parameters. The clinician programmer generally includes a user interface which may be a graphical user interface and can further include audio and haptic features as well. The clinician programmer 60 may be configured with specialized software applications, for example, the specialized alignment software that determines and outputs an alignment indicator to guide a user through a fine-tuned charging device alignment procedure. As noted above, the clinician programmer can include a module with hardware and computer-code to execute analysis of charging parameters for determining charging efficiency, where the module may be a component of the control unit microprocessor, a pre-processing unit coupled to or in-line with the stimulation and/or sensory cables, or the like. In this embodiment, the clinician program 60 communicates directly with the charging device 50 and obtains one or more charging parameters during charging. The clinician programmer 60 provides the alignment indicator 65, which may be a dynamically updated display of the charging parameters or associated metric (e.g., charging efficiency) to enable the clinician to observe the strength of efficiency of charging during manual adjustment of the position of the charging device 50. In one aspect, the charging device is communicatively coupled to the clinician programmer 60 by shortwave radio communication (e.g., Bluetooth), while currently communicating to the implantable pulse generator through another communication scheme (e.g., MedRadio). In some embodiments, the clinician programmer 60 obtains the one or more charging parameters from the charging device 50 but does not otherwise modify the charging operation based on alignment determinations. In some embodiments, the alignment indicator 65 can further provide a spatial illustration of the position of the charging device relative the implantable medical device. In other embodiments, the clinician programmers can utilize various other means of indicating alignment, including but not limited to haptic, visual (e.g., LED, graphic), or audio (e.g. beep or alert) to indicate optimization of alignment. In some embodiments, the indicator can include multiple different types of notifications or a notification that changes as the charging device is adjusted and nears optimal placement. The alignment indicator, including any of the features noted above, may be incorporated into the charging device itself, or may be provided on another user device, for example a device of the patient, such as the patient remote or a personal computing device (e.g., smartphone, tablet). Each of the above aspects described with respect to the clinician programmer may be similarly applied to the specialist user device 90, which can communicate with either the patient's standard charging device 50 or the specialized charging device 95.

Figure 2A:
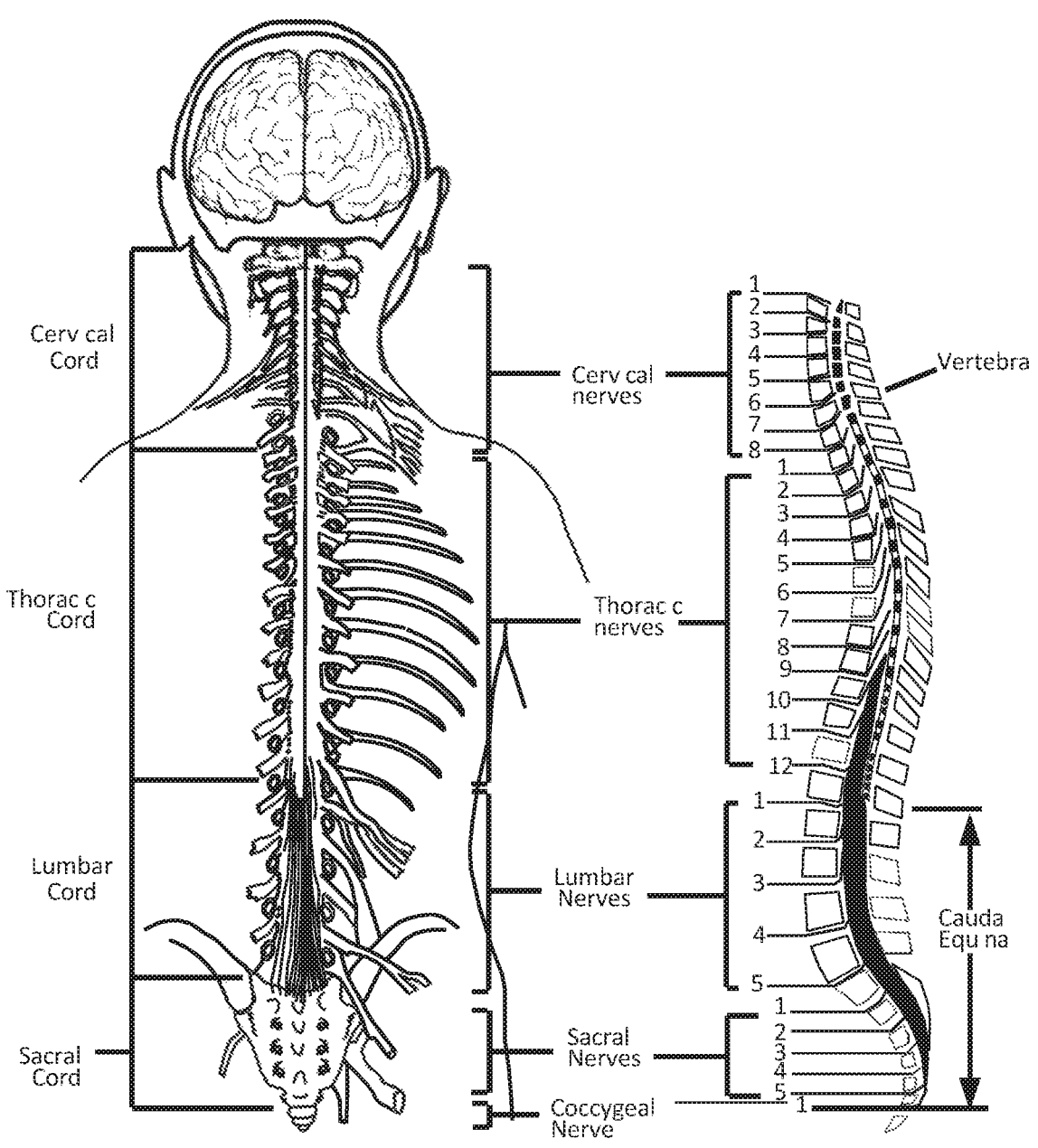
FIGS. 2A-2C show diagrams of the nerve structures along the spine, the lower back and sacrum region, which may be stimulated in accordance with some embodiments.
Figure 2B:
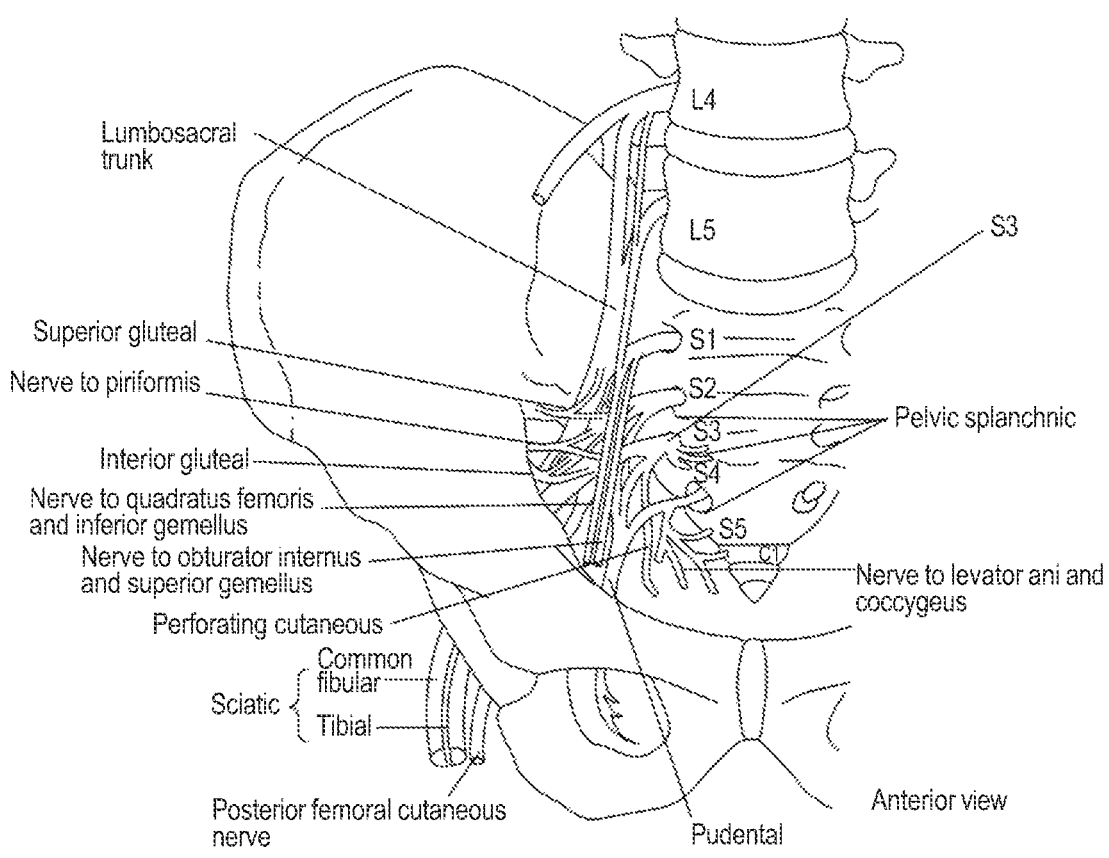
Figure 2C:
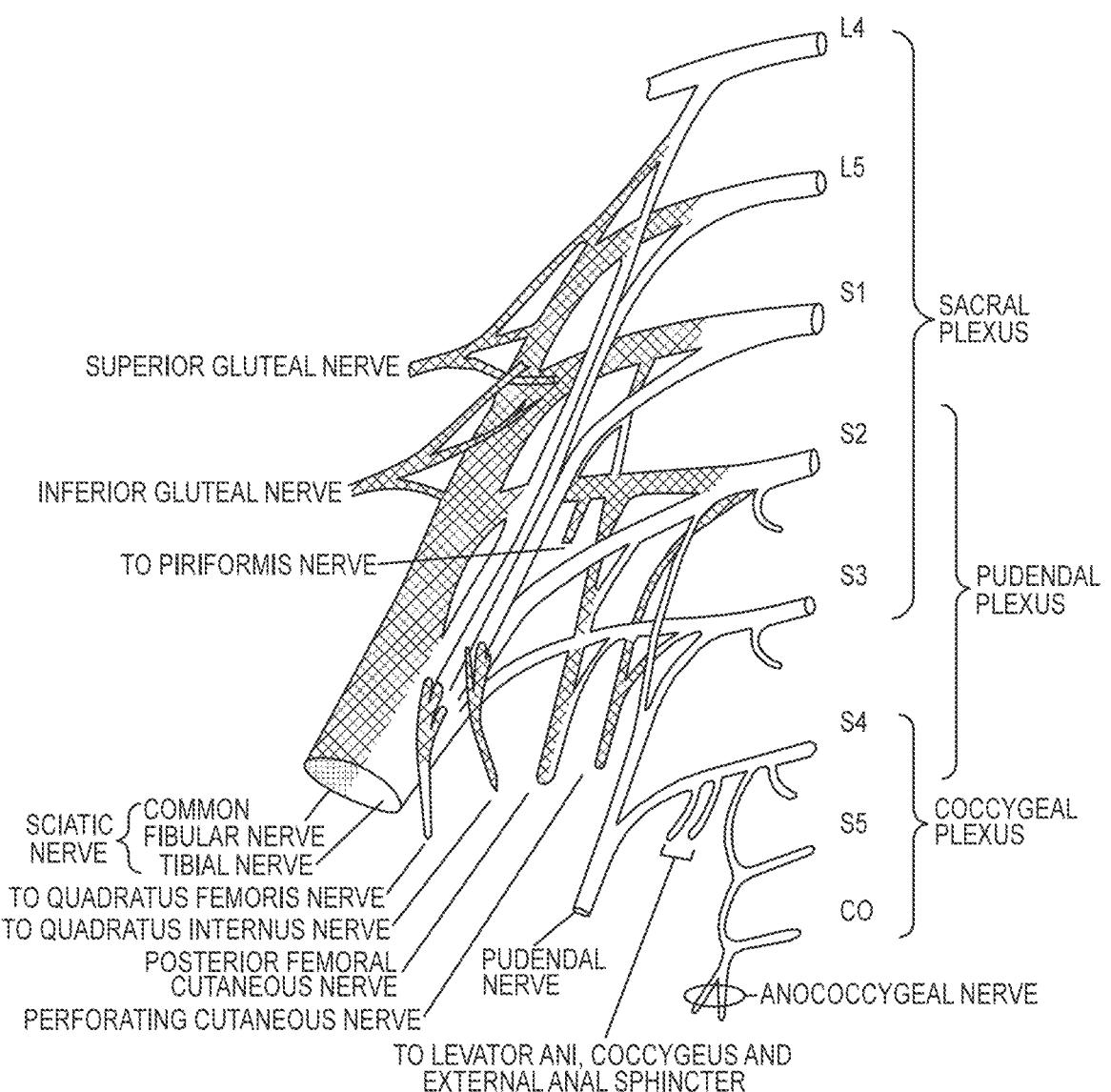

FIGS. 2A-2C show diagrams of various nerve structures of a patient, which may be used in neurostimulation treatments. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, either visually, using EMG as described herein or both, the physician can determine whether the targeted nerve is being stimulated. While stimulation at a certain threshold may trigger the noted muscle responses, stimulation at a sub-threshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder-related dysfunction, and in particular OAB.

FIG. 3 schematically illustrates an example of a fully implanted neurostimulation system 110 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, similar systems may be used in treating patients with, for example, chronic, severe, refractory neuropathic pain originating from peripheral nerves or various urinary dysfunctions or still further other indications. Implantable neurostimulation systems may be used to either stimulate a target peripheral nerve or the posterior epidural space of the spine.

As shown in FIG. 3, the implantable pulse generator 10 of the INS is implanted in the lower back, upper buttock region of the patient. Patients are commonly instructed to position the charging device over a scar from the incision formed during implantation of the neurostimulator. However, the location of the scar in a sacral neurostimulation system implantation makes this task difficult since the patient cannot readily observe the scar during placement of the charging device. Further, in some patients, the location of the neurostimulator may change over time, for example due to weight loss that tends to occur after successful treatment. Thus, by locating the alignment indicator feature within a user device, such as a clinician programmer, patient remote, patient device or specialist device, the alignment indicator may be communicated to the user during manual positioning of the charging device, thereby allowing for precise placement without visually observing the location of the IPG. While the scar might fail to indicate a proper position for the charging device, the scar may still be used as a reference with respect to the newly determined optimal position (e.g. 2 cm up/3 cm to the right from the scar), which may be communicated to the patient for subsequent charging sessions.

Properties of the electrical pulses may be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3, the implantable neurostimulation system 110 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 110.

Figure 4:
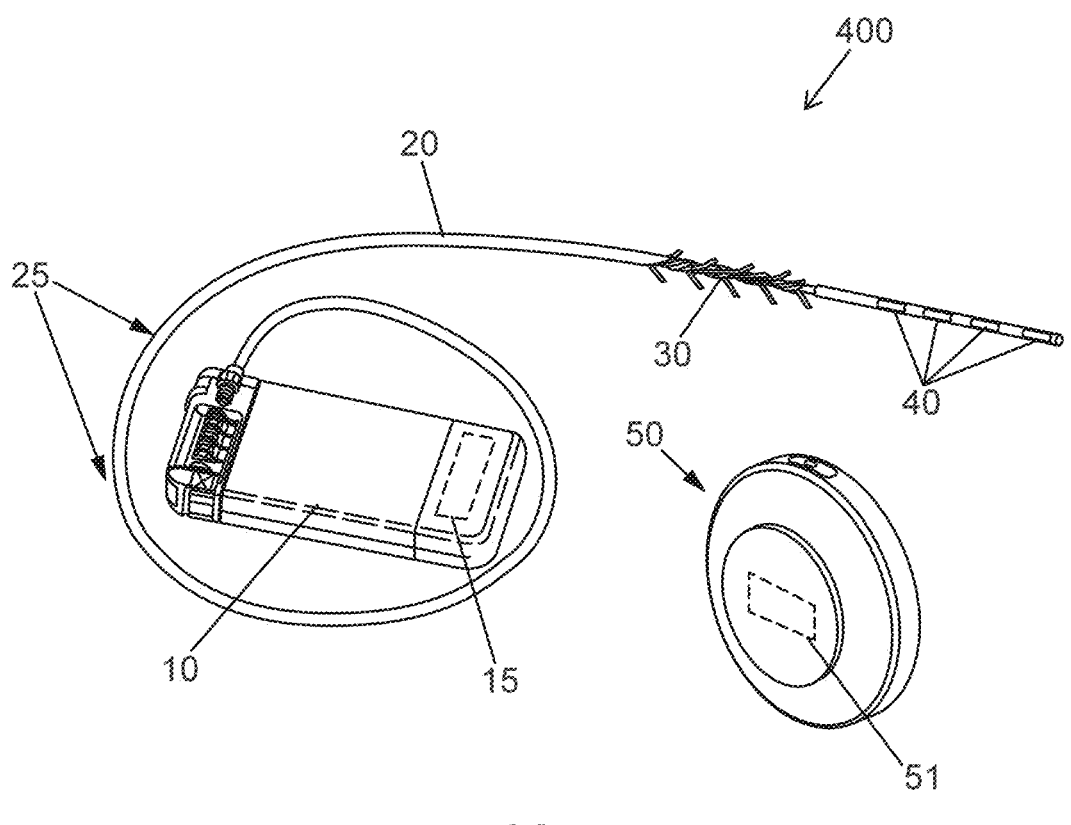
FIG. 4 shows an example of a neurostimulation system having an implantable stimulation lead, an implantable pulse generator, and an external charging device, in accordance with some embodiments.

FIG. 4 illustrates an example neurostimulation system 400 that is fully implantable and adapted for sacral nerve stimulation treatment. The implantable system 400 includes an IPG 10 that is coupled to a neurostimulation lead 20 that includes a group of neurostimulation electrodes 40 at a distal end of the lead and an internal receiving coil 15. The lead includes a lead anchor portion 30 with a series of tines extending radially outward to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

In one aspect, the IPG is rechargeable wirelessly through conductive coupling by use of a charging device 50, which is a portable device powered by a rechargeable battery to allow patient mobility while charging. The charging device includes a charging coil 51 disposed within and is used for transcutaneous charging of the IPG through RF induction. The charging device 50 can either be either patched to the patient's skin using an adhesive or may be held in place using a belt 53 or by an adhesive patch 52. When recharging the IPG 10, the charging device 50 may be held in place using the belt 53 or adhesive patch 52 such that a surface 54 of the charging device 50 contacts the skin through which the IPG 10 is recharged, is parallel to the skin through which the IPG 10 is recharged, and/or is proximate to the skin through which the IPG 50 is recharged. In such position, the charging device axis, which may be perpendicular to the surface 54 may be perpendicular to the skin through which the IPG 10 is recharged. The charging device 50 may be charged by plugging the charging device directly into an outlet or by placing the charging device in a charging dock or station that connects to an AC wall outlet or other power source.

The charging device 50 can include a housing. The housing can comprise a variety of shapes and sizes. In some embodiments, the housing may be cylindrically shaped as shown in FIG. 4, and specifically, can comprise a plurality of connected cylindrical portions, wherein the connected cylindrical portions have different diameters and/or lengths. In some embodiments, the housing 51 may be a metal or polymer such as a plastic or the like.

The charging device 50 can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. The charging device 50 may include an energy storage feature, such as one or more capacitors, and typically includes a wireless charging unit. Some details of charging device 50 will be discussed at greater lengths below with respect to FIG. 7. The charging device can further include one or more positional sensors, such as an accelerometer, for determination of a relative position of the charging device and/or a direction of movement during repositioning. Any of the above features of the charging device 50 may be shared by the specialized charging device 95 (see also FIGS. 29-30). Preferably, the specialized charging device includes charging coils of the same size, shape and arrangement as standard charging device 50 such that any optimal position of the specialized charging device corresponds exactly to the standard charging device 50.

The system may further include a patient remote 70 and clinician programmer 60, each configured to wirelessly communicate with the implanted IPG, or with the EPG during a trial. The clinician programmer 60 may be a tablet computer used by the clinician to program the IPG and the EPG. The device also includes the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figures 5A, 5B:
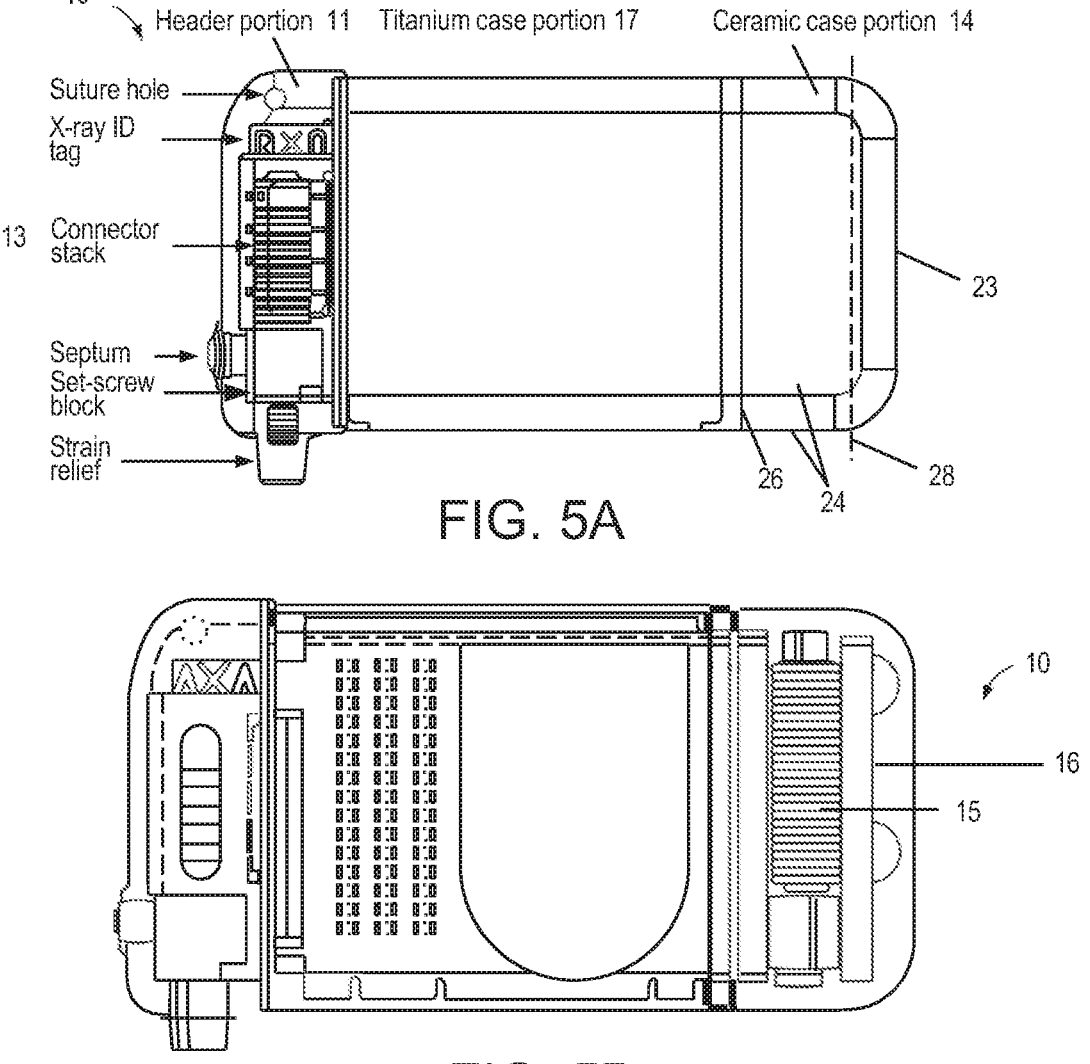
FIGS. 5A-5B show detail views of an implantable pulse generator and associated components for use in a neurostimulation system, in accordance with some embodiments.

FIG. 5A-5B show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses have a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses may be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 10 includes a controller having one or more pulse programs, plans, or patterns that may be created and/or pre-programmed. In some embodiments, the IPG may be programmed to vary stimulation parameters including pulse amplitude in a range from 0 mA to 10 mA, pulse width in a range from 50 us to 500 μs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. This allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed-through assembly 12 and connector stack 13, while the ceramic case portion 14 houses an antennae assembly 16 to facilitate wireless communication with the clinician program, the patient remote, and/or a charging coil to facilitate wireless charging with the charging device. The remainder of the IPG is covered with a titanium case portion 17, which encases the printed circuit board, memory and controller components that facilitate the electrical pulse programs described above. The ceramic portion 14 includes an end 23, sides 24, and a connection portion 26 that connects the ceramic portion 14 to the case portion 17. In the example shown in FIG. 5B, the antennae assembly 16 is positioned such that a plane 28, in which loops of a radiating element lay, is perpendicular to and extends through the sides 24 of the ceramic portion 14.

In some embodiments, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (e.g., 3 mol percent Yttria-stabilized tetragonal Zirconia Polycrystals) ceramic, which has a high flexural strength and impact resistance and has been commercially utilized in a number of implantable medical technologies. However, other ceramics or other suitable materials may be used for construction of the IPG, and ceramic may be used to form additional portions of the case.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at a depth of 3 cm with the charging device, when positioned on a skin surface of the patient near the IPG, and reduces re-charging time.

Figure 6:
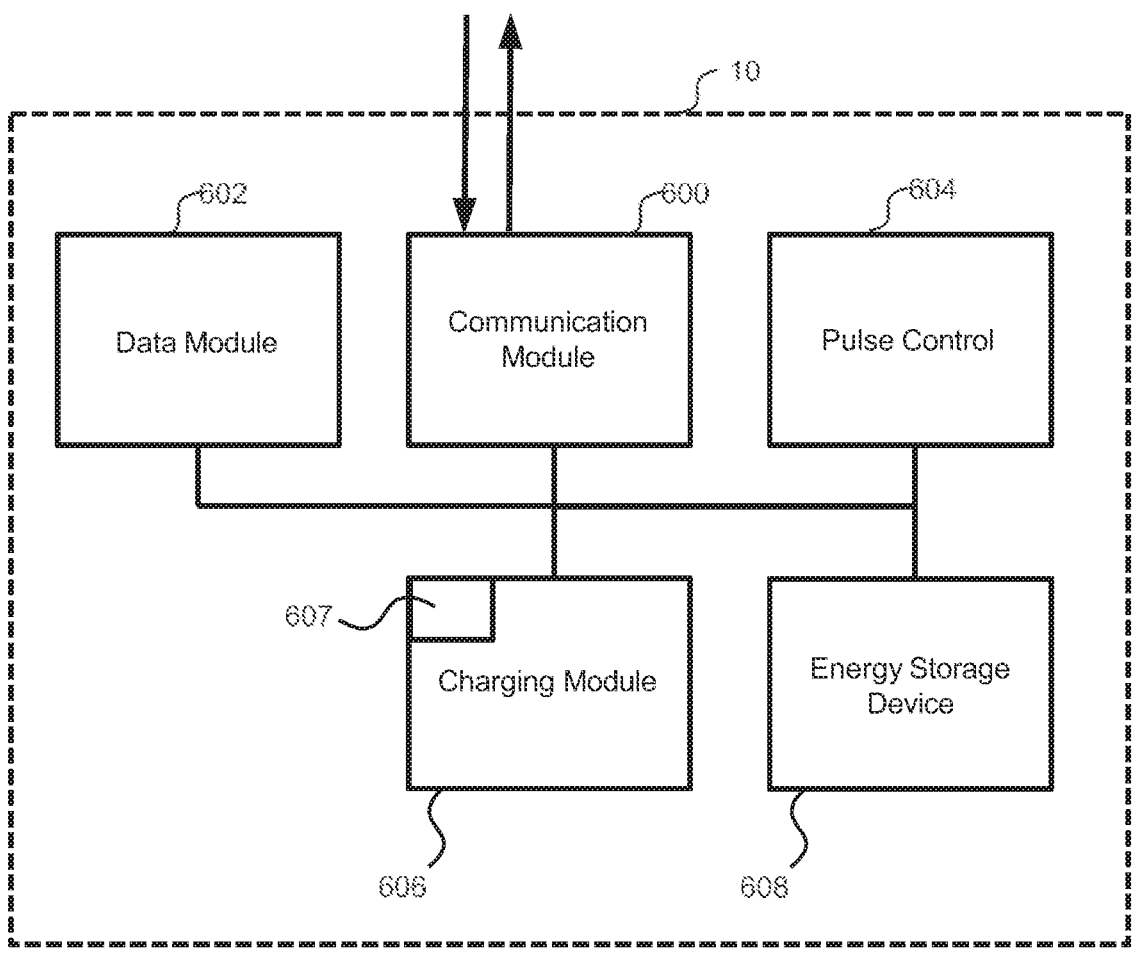
FIG. 6 shows a schematic illustration of one embodiment of the architecture of the IPG, in accordance with some embodiments.

FIG. 6 shows a schematic illustrating one embodiment of the architecture of the IPG 10. In some embodiments, each of the components of the architecture of the IPG 10 may be implemented using the processor, memory, and/or other hardware component of the IPG 10. In some embodiments, the components of the architecture of the IPG 10 can include software that interacts with the hardware of the IPG 10 to achieve a desired outcome, and the components of the architecture of the IPG 10 may be located within the housing.

In some embodiments, the IPG 10 can include, for example, a communication module 600. The communication module 600 may be configured to send data to and receive data from other components and/or devices of the exemplary nerve stimulation system including, for example, the clinician programmer 60, the charging device 50, and/or the patient remote 70. In some embodiments, the communication module 600 can include one or several antennas and software configured to control the one or several antennas to send information to and receive information from one or several of the other components of the IPG 10. In some embodiments, for example, when connecting with the charging device 50, the communications module 600 may be configured to send data identifying the IPG 10 and/or characterizing one or several attributes of the IPG 10. In some embodiments, this information may be, for example, a number uniquely identifying the IPG 10 such as, for example, a serial number, or the like. In some embodiments, this data can characterize one or several attributes of the IPG 10 such as, for example, the natural frequency of a charging module 606 of the IPG 10 and/or of one or several components of the charging module 606 of the IPG. In some embodiments, the IPG 10 may be configured to communicate one or more charging parameters to a user device during charging, including any of a clinician programmer, patient remote, or a portable patient computing device, on which an alignment indicator may be provided based on the one or more charging parameters.

The IPG 10 can further include a data module 602. The data module 602 may be configured to manage data relating to the identity and properties of the IPG 10. In some embodiments, the data module can include one or several databases that can, for example, include information relating to the IPG 10 such as, for example, the identification of the IPG 10, one or several properties of the IPG 10, or the like. In one embodiment, the data identifying the IPG 10 can include, for example, a serial number of the IPG 10 and/or other identifier of the IPG 10 including, for example, a unique identifier of the IPG 10. In some embodiments, the information associated with the property of the IPG 10 can include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like. In some embodiments, the information associated with the property of the IPG 10 can include, for example, data identifying the natural frequency of the IPG 10 and/or components thereof. In some embodiments, this information identifying the natural frequency may be generated at the time of the manufacture of the IPG 10.

The IPG 10 can include a pulse control 604. In some embodiments, the pulse control 604 may be configured to control the generation of one or several pulses by the IPG 10. In some embodiments, for example, this may be performed based on information that identifies one or several pulse patterns, programs, or the like. This information can further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information can specify aspects of a pulse pattern and/or pulse program, such as, for example, the duration of the pulse pattern and/or pulse program, and/or the like. In some embodiments, information relating to and/or for controlling the pulse generation of the IPG 10 may be stored within the memory.

The IPG 10 can include a charging module 606. In some embodiments, the charging module 606 may be configured to control and/or monitor the charging/recharging of the IPG 10. In some embodiments, for example, the charging module 606 can include one or several features configured to receive energy for recharging the IPG 10 such as, for example, one or several inductive coils/features that can interact with one or several inductive coils/features of the charging device 50 to create an inductive coupling to thereby recharge the IPG 10. In some embodiments, the charging module 606 can include hardware and/or software configured to monitor the charging of the IPG 10 including, for example, the charging coil assembly 15, also referred to herein as the receiving coil assembly 15 or the elongate receiving coil assembly 15. In some embodiments, the software of the charging module may be updated periodically, for example in a software push through an external computing device in communication with the communication module. Typically, the communication module provides a secure, authentication of any communication regarding a software update such that any software update is communicated only if a secure, authenticated communication is received, for example, a communication from an authorized clinician programmer or a communication with an authorization key from a network or remote server.

The charging module 606 of the IPG 10 can include a charging circuit 607, also referred to herein as the resonant circuit 607, the secondary charging circuit 607, the secondary resonant circuit 607, the receiving charging circuit 607, or the receiving resonant circuit 607. In some embodiments, the charging circuit 607 can comprise, for example, at least one of: an inductor; a capacitor; or a resistor. The charging circuit 607 may be characterized by a natural frequency, which natural frequency may be determined at, for example, the time of assembly of the charging circuit 607 or after the implantation of the IPG 10 in the body. In some embodiments, because of the relatively constant temperature and environment in the body, the natural frequency of the charging circuit 607 can remain constant after the implantation of the IPG 10 into the body. The IPG 10 can further include an energy storage device 608, which in this embodiment is a rechargeable battery configured to receive charging energy from the charging module 606.

Figure 7:
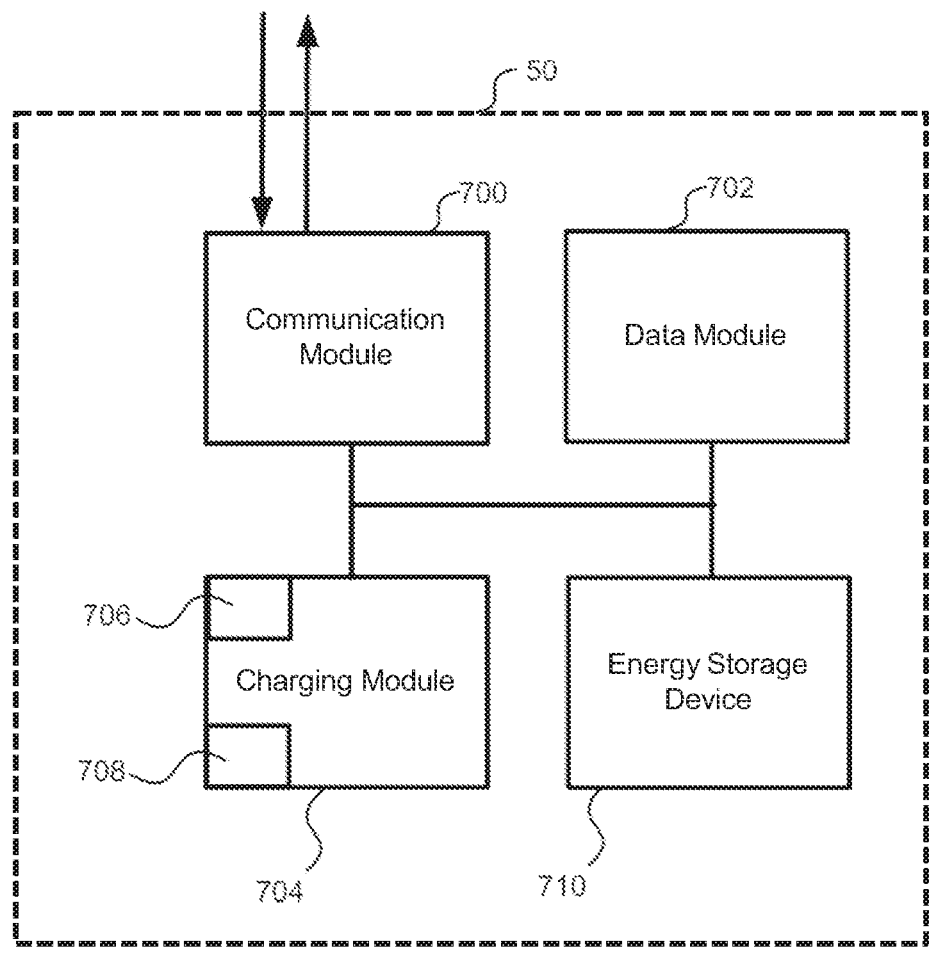
FIG. 7 shows a schematic illustration of one embodiment of the architecture of the charging device, in accordance with some embodiments.

FIG. 7 shows a schematic illustration of one embodiment of the architecture of the charging device 50. The features described in the following paragraphs can similarly be applied to the specialized charging device 95. In some embodiments, each of the components of the architecture of the charging device 50 may be implemented using the processor, memory, and/or other hardware component of the charging device 50. In some embodiments, the components of the architecture of the charging device 50 can include software that interacts with the hardware of the charging device 50 to achieve a desired outcome, and the components of the architecture of the charging device 50 may be located within the housing 51.

In some embodiments, charging device 50 can include, for example, a communication module 600. The communication module 700 may be configured to send data to and receive data from other components and/or devices of the exemplary nerve stimulation system including, for example, the clinician programmer 60, the IPG 10, and/or the patient remote 70. In some embodiments, the communication module 700 can include one or several antennas and software configured to control the one or several antennas to send information to and receive information from one or several of the other components of the charging device 50. In some embodiments, the charging device communicates with the IPG during charging with a first antennae and communicates one or more charging parameters or associated metric to the user device by a second antenna. In some such embodiments, the first antenna can communicate with the IPG by MedRadio, while the second antenna communicates with the user device by Bluetooth. In some embodiments, when connecting with the IPG 10, the communications module 700 may be configured to receive data identifying the IPG 10 and/or characterizing one or several attributes of the IPG 10. In some embodiments, this information may be, for example, a number uniquely identifying the IPG 10 such as, for example, a serial number, or the like.

The charging device 50 can further include a data module 702. The data module 702 may be configured to manage data relating to the identity and properties of the IPG 10. In some embodiments, the data module can include one or several databases that can, for example, include information relating to the IPG 10 such as, for example, the identification of the IPG 10, one or several properties of the IPG 10, or the like. In one embodiment, for example, the data module can comprise a database including one or several IPG 10 identifiers such as serial numbers for those one or several IPGs 10. In some embodiments, the data module 702 can further include characterization data associated with some or all of the one or several IPGs 10 identified in the data module 702. In some embodiments, for example, this characterization data can include the identification of the natural frequency of charging circuit 607 of the IPG 10. In some embodiments, this characterization data may be received from the IPG 10 and/or may be generated by the charging device 50 in response to interactions with the IPG 10. In some such embodiments, the data modules provide segregation of data, for example, between charging parameters utilized during charging control and charging parameters sent to a user device. Such an approach may allow the user device to access data and processes that would not otherwise be feasible or recommended, to avoid unauthorized access to charging control operations by the patient or clinician.

The charging device 50 can include a charging module 704. In some embodiments, the charging module 704 may be configured to control and/or monitor the charging/recharging of the IPG 10. In some embodiments, for example, the charging module 704 can include one or several features configured to provide energy for recharging the IPG 10 such as, for example, one or several inductive coils/features that can interact with one or several inductive coils/features of the IPG 10 to create an inductive coupling to thereby recharge the IPG 10. In some embodiments, the charging module 704 can include hardware and/or software configured to monitor the charging of the IPG 10 including, for example, the charging coil assembly 15.

The charging module 704 of the charging device 50 can include a charging circuit 706, also referred to herein as the resonant circuit 706, the primary charging circuit 706, the primary resonant circuit 706, the transmitter charging circuit 706, or the transmitter resonant circuit 706. In some embodiments, the charging circuit 706 can include, for example, at least one of: an inductor; a capacitor; or a resistor. In some embodiments, the resonant circuit 706 can include the sending coil assembly, also referred to herein as a transmitting coil assembly or a primary coil assembly.

In some embodiments, the charging module 704 can include a driver 708. The driver 708 may be, for example, a non-class E driver, and in some embodiments, the driver 708 may be a class E driver, and specifically may be a microprocessor-controlled class E driver as disclosed in U.S. patent application Ser. No. 14/446,294, filed on Jul. 29, 2014, the entirety of which is hereby incorporated by reference herein. In some embodiments, the driver 708 may be configured to provide electrical pulses to the resonant circuit 706 to thereby charge the IPG 10. In some embodiments, the driver 708 may be further configured to provide these pulses at a frequency corresponding to the natural frequency of the resonant circuit 706. Thus, in some embodiments, the natural frequency of the resonant circuit 706 of charging device 50 may be determined by determining the frequency with which driver 708 is providing pulses to the resonant circuit 706.

The charging device 50 can include an energy storage device 710. The energy storage device 710 may be any device and/or features configured to store energy and can include, for example, one or several batteries, capacitors, fuel cells, or the like. In some embodiments, the energy storage device 710 may be configured to provide charging energy to the charging module 704 for charging of the IPG 10. In this embodiment, the energy storage device 710 is a rechargeable battery that is recharged inductively by a charging dock in which the charging device may be stored when not in use.

In some embodiments, for example in which the IPG 10 is implanted such that at least one of axes 802, 809 is parallel and/or substantially parallel with the skin surface closest to the IPG 10 and/or from which charging of the IPG 10 is intended, the use of a planar winding 852 in the charging device 50 combined with an elongate winding 800 in the IPG 10 can eliminate the need to control the rotational orientation of the charging device 50 with respect to the IPG 10. This can simplify the positioning of the charging device 50 with respect to the IPG 10. Specifically, the effect of the relative rotational orientation of the charging device 50 with respect to the IPG 10 is diminished when the IPG 10 and the charging device 50 have a relative orientation such that the axes 802, 809 of the charging circuit 15 of the IPG 10 are nonparallel to the winding axis 854 and/or the core axis 864, and/or have a relative orientation such that the axes 802, 809 of the charging circuit 15 of the IPG 10 are perpendicular and/or substantially perpendicular to the winding axis 854 and/or the core axis 864. In such an embodiment, effective energy transfer between from the charging device 50 to the IPG 10 may be achieved by positioning the charging device 50 proximate to the IPG 10 without having to also control the rotational orientation of the charging device 50 about the charging device axis 55. As rotational orientation of the charging device 50 does not need to be controlled, the positioning of the charging device 50 for recharging of the IPG 10, and thus recharging of the IPG 10 is simplified.

As a part of positioning, or subsequent to positioning of the charging device 50 with respect to the IPG 10, the charging device 50 can power the sending coil assembly 850, and specifically, the charging module 704 can power the sending coil assembly 850. In some embodiments, this powering of the sending coil assembly 850 can include the generation of series of pulses by the driver 708, the pulses being timed to cause resonance in the charging circuit 706. These pulses are then delivered to the charging circuit 706 to generate resonance in the charging circuit 706 at the resonant frequency of the charging circuit 706 and/or at another desired frequency. Through this powering of the charging circuit 706, and the current oscillations at the charging circuit 706, a magnetic field may be generated by the sending coil assembly 850. The magnetic field may be directed away from the circuitry 870 of the charging device 50 by the core 862 of the sending coil assembly 850. The magnetic field may be generated until the charging device 50 determines to terminate charging of the IPG 10 and/or until the charging device 50 is instructed to terminate charging of the IPG 10. Thus, the charging operation during which positioning of the charging device is performed may be standard operating charging or may be a modified charging operation especially suited for placement of the charging device, for example, as described above.

Figure 8:
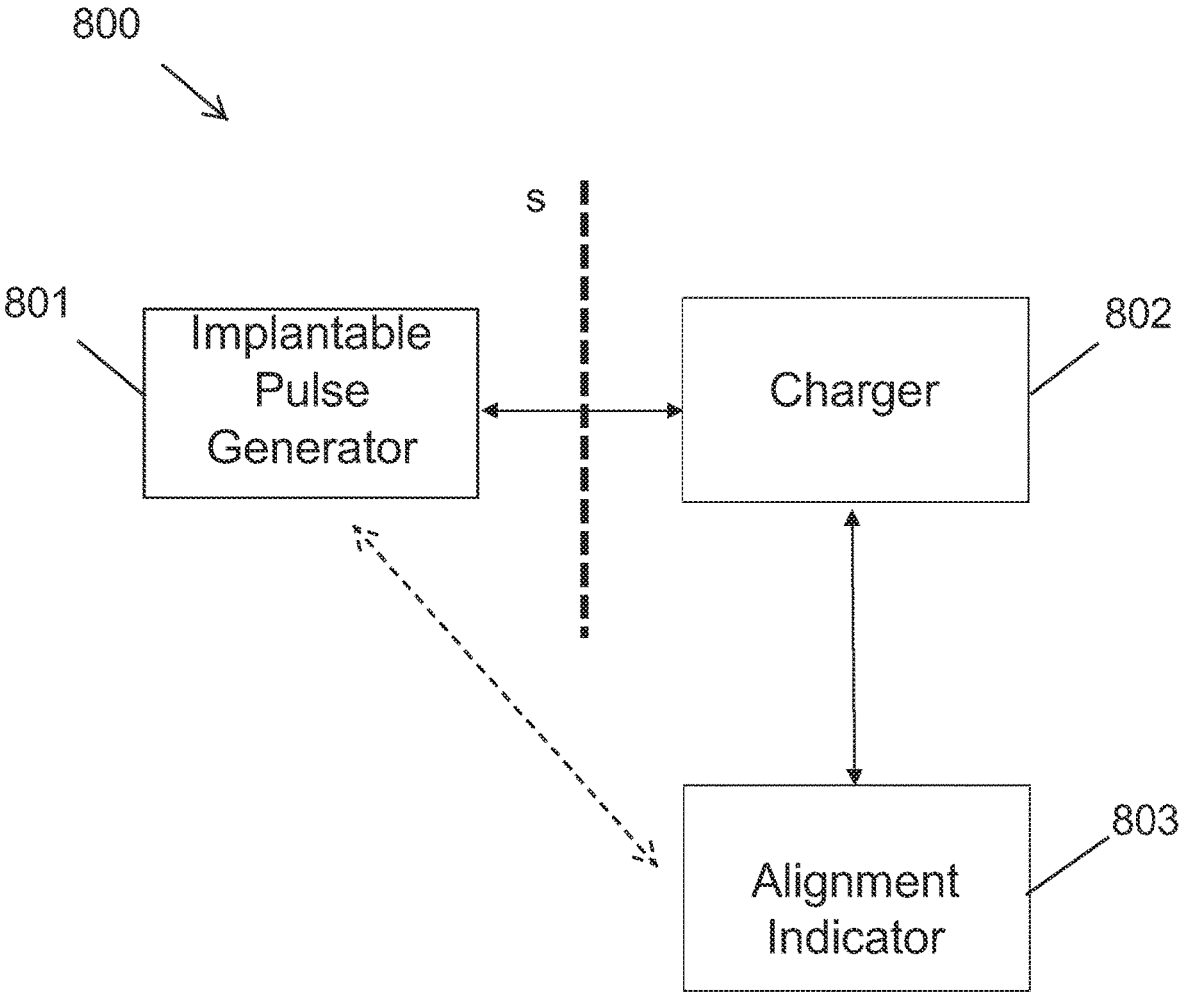
FIG. 8 shows a schematic illustration of communication between an IPG and charging device and an alignment indicator, in accordance with some embodiments.

FIG. 8 shows a schematic illustration of a system 800 having an IPG 80, charging device 802 (e.g., standard or specialized) and an alignment indicator 803, in accordance with some embodiments. In this embodiment, the charging device 802 communicates directly with the implantable pulse generator 801 across the patient's skin to facilitate controlled transcutaneous energy transfer between the charging device and implantable device. Typically, this transcutaneous communication is performed by shortwave radio transmissions (e.g., MedRadio). The charging device 801 then communicates one or more charging parameters to the alignment indicator 803, which may be displayed on a user interface of one or more external computing devices or may be integrated within the charging device itself. Typically, this latter communication is by another type of shortwave radio transmission (e.g., Bluetooth). In some embodiments, the alignment indicator utilizes information obtained only from the charging device, which includes charging parameters from both the charging device and the implantable pulse generator during charging. In some embodiments, the alignment indicator can also include information obtained directly from the implantable pulse generator, or information obtained from both.

Figure 9:
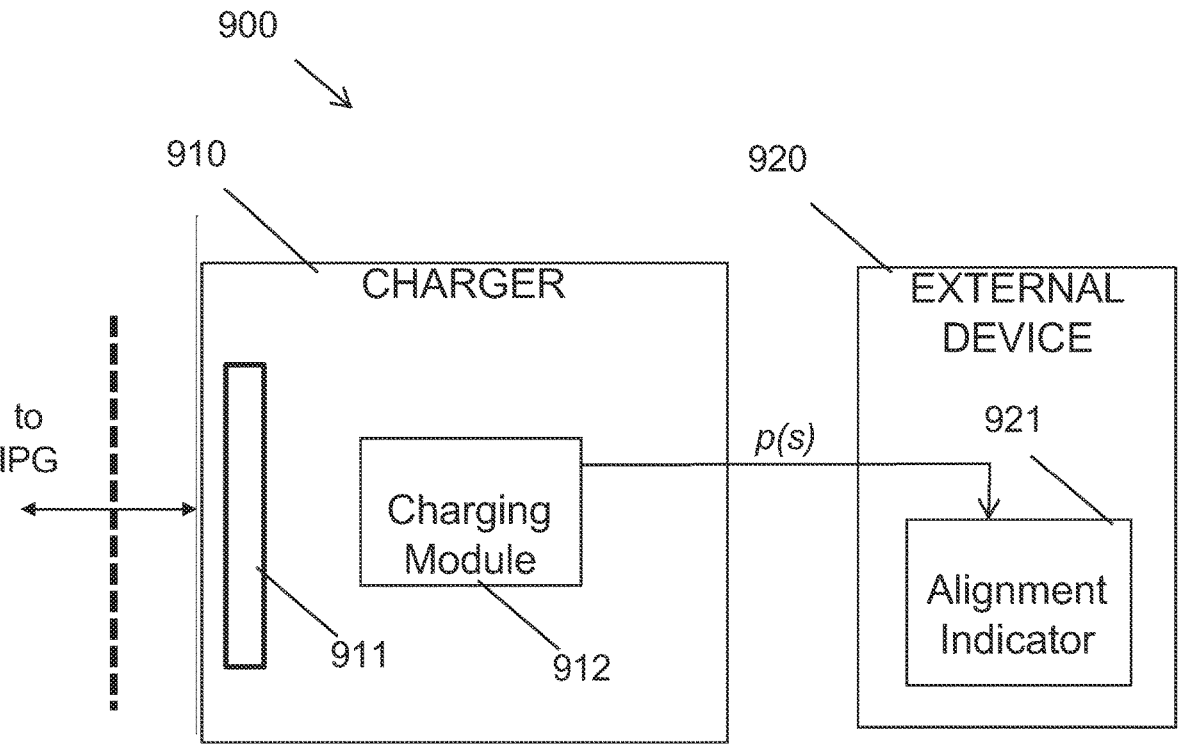
FIG. 9 shows a schematic illustration of a charging device communicating with an external device having an alignment indicator, in accordance with some embodiments.

FIG. 9 shows a schematic illustration of system 900 having a charging device 910 with a charging coil 911 and charging module 912 having circuitry and a processor configured to control transcutaneous charging with the IPG. The charging module 912 is further configured to communicate one or more charging parameters, p(s), during charging to an external user device 920 upon receiving a request from the external device. The external device 902 indicates alignment on a user interface as alignment indicator 921. The indicator can include any of an audio, visual, or haptic output on the user interface of the external device 920. In some embodiments, the external user device 920 is associated with a specialist (e.g., field technician, device provider representative), while in other embodiments, the user device may be associated with a clinician (e.g., clinician programmer) or may be associated with the patient (e.g., patient remote, smartphone, table). In this embodiment, the alignment indicator may be a display of the charging parameters or associated metric obtained directly from the charging module (e.g., charging signal strength, charging efficiency, current, voltage, etc.). In some embodiments, these parameters or metric may be a parameter or metric that is already obtained and determined by the charging module during standard charging operation such that further processing of the parameters or metric by the external device is not required.

Figure 10:
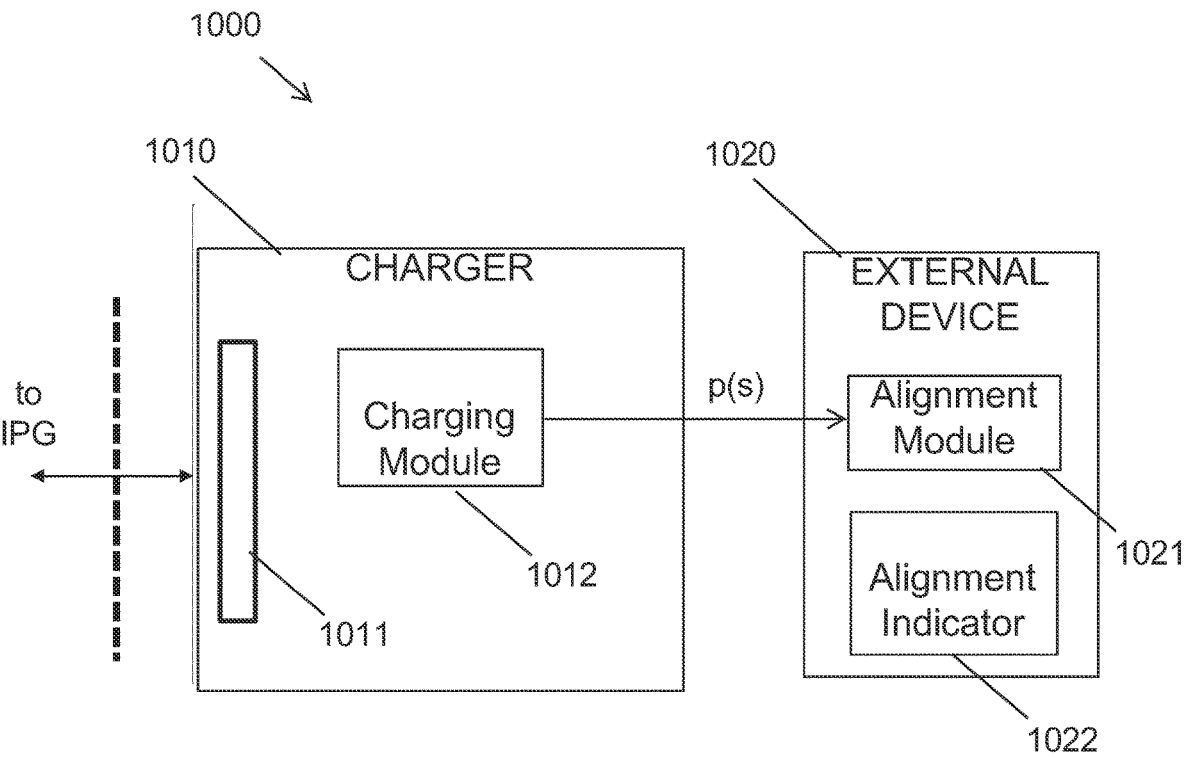
FIGS. 10-11 show schematic illustrations of charging devices communicating with external devices having an alignment indicator, in accordance with some embodiments.

FIG. 10 shows a schematic illustration of system 1000 having a charging device 1010 with charging coil 1011 and charging module 1012 having circuitry and processor configured to control transcutaneous charging with the IPG. The charging module 912 is further configured to communicate one or more charging parameters, p(s), during charging to an external device 1020. The external device 1020 indicates alignment on a user interface as alignment indicator 1022. The indicator can include any of an audio, visual, or haptic output on the user interface of the external device 920. In some embodiments, the external user device 1020 is associated with a specialist, while in other embodiments, the device is associated with the clinician or the patient. In this embodiment, the external device further includes an alignment module 1021 that is configured to receive the charging parameters and process the parameters into a useful metric, such as charging efficiency, or to determine the suitable alignment indicator based on the one or more charging parameters.

Figure 11:
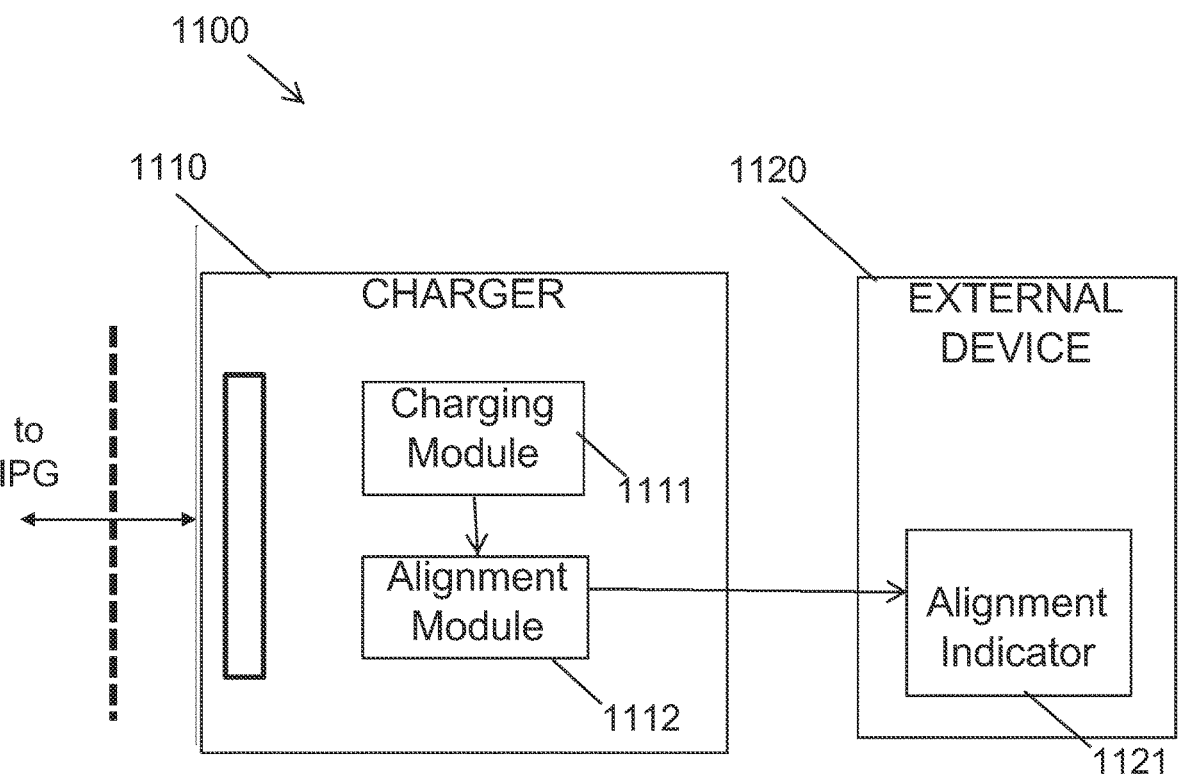

FIG. 11 shows a schematic illustration of a charging device 1110 having a charging module 111 and external device 1120 with alignment indicator 1121 that operates in substantially the same or similar manner as that in FIG. 10, except the alignment module 1112 is included within the charger 1110. In some embodiments, this functionality is provided by a software push update to the charger from the external device.

Figure 12:
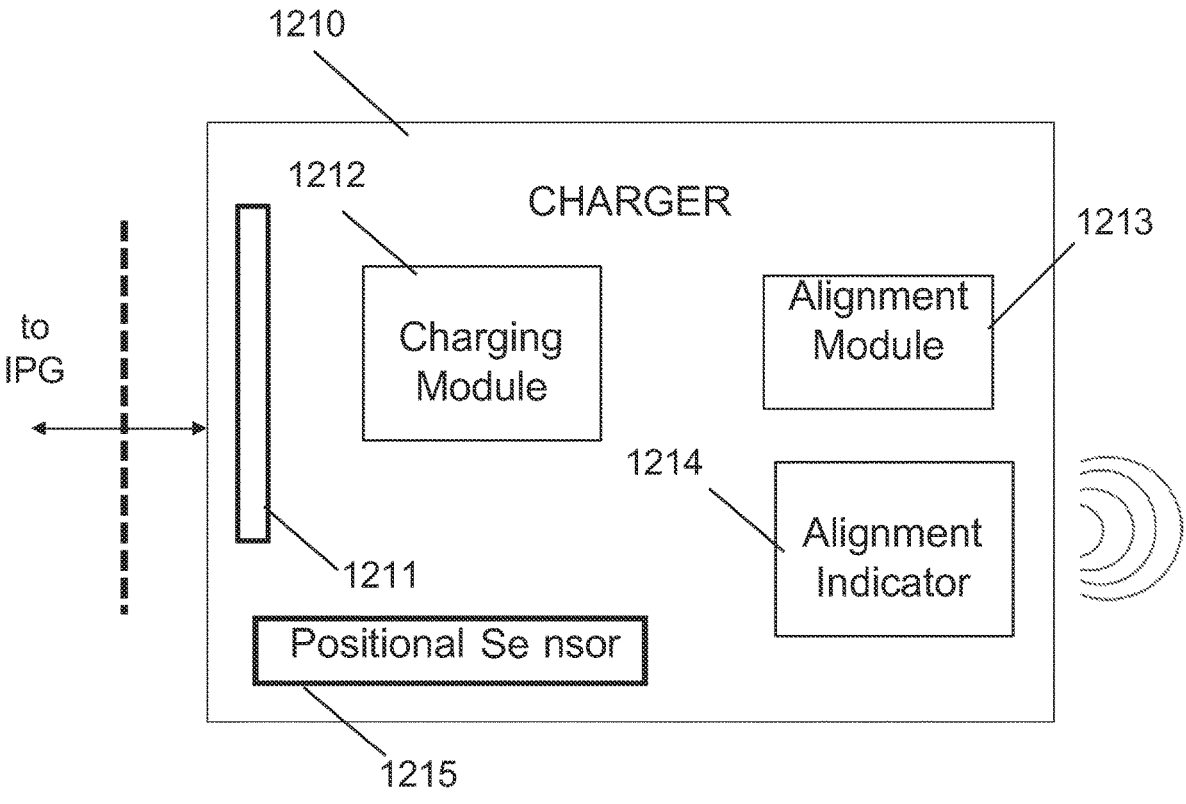
FIG. 12 shows a depiction of a charging device having an integrated alignment indicator and positional sensor, in accordance with some embodiments.

FIG. 12 shows a schematic illustration of a charging device integrated with the alignment indicator. Charger 1210 includes a charging module 1212, alignment module 1213 and alignment indicator 1214 that operates in a similar manner as in previous embodiments, except the output of the alignment indicator is provided by the charger itself. The indicator can include any of: an audio, visual, or haptic output on the user interface of the external device 920. In some embodiments, the indicator is an audio output, such as a series of beeps or tones, or audio verbal instructions to the user. In this embodiment, it may be advantageous to use different types of indicator alerts, or an adaptive alert based on the charging parameters, for example, a series of beeps that increase in frequency as the charging efficiency increases and/or changes to a sustained beep when maximum charge efficiency is detected to indicate the optimal charging device position.

In another aspect, the charging device can include one or more positional sensors 1215, such as an accelerometer, the output from which may be used to determine a relative position or movement of the charging device during manual positioning of the charging device. The positional sensors may be included in any of the embodiments described herein. The output from the one or more sensors may be utilized to determine specific directional guidance to the user or clinician, for example, instruction to move the charging device upwards, left, or right to improve alignment. In some embodiments, the sensor may be identify a rotational orientation of the charging device so that a user can receive instruction to rotate the charging device to further align corresponding coils. It is noted that the adhesive attachment device and belt allow for rotation of the charging device while supported within, as described in U.S. Pat. No. 10,682, 521, which is incorporated herein by reference in its entirety. In some embodiments, the attachment device can further include one more sensors so that a relative position and/or orientation of the charging device within may be determined from the sensor positional output.

In another aspect, the subject matter pertains to specialized application configured to operate on an external user device in communication with the charging device and/or implantable pulse generator. In some embodiments, the external user device may be any of a specialist device, a clinician programmer, a patient remote or other specialized medical equipment associated with the neurostimulation system. In some embodiments, the external computing device may be a standard computing device associated with the specialist, the clinician, or the patient, such as a smartphone, tablet, laptop, or desktop computer, where the functionality to perform the methods described herein are provided, at least in part, by operation of the specialized application embodied by executable instructions recorded on a memory of the respective user device.

FIGS. 13-18 shows example screen views of a user device within a specialized application having an alignment indicator within a user device, in accordance with some embodiments. The specialized application executes a charging device alignment procedure by which the specialist or clinician can observe fine-tuned alignment while the user manually adjusts the position of the charging device. This procedure may be used during initial setup of the system with the patient, and as needed, or at any subsequent time to troubleshoot charging issues, such as when patient experiences sub-optimal charging performance due to migration of the implanted charger or significant weight loss.

Figure 13:
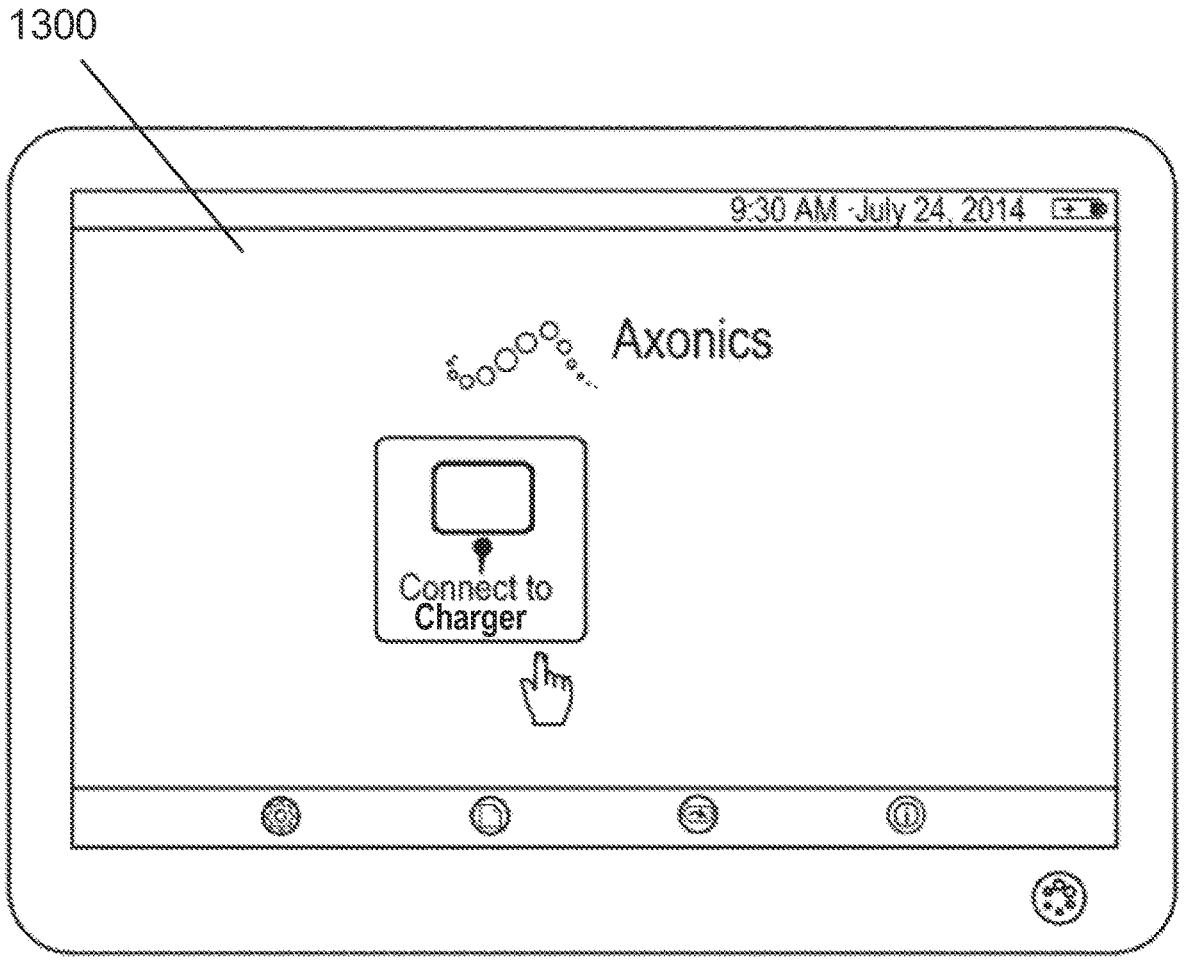
FIG. 13-18 shows example screen views of a user device performing a fine-tuned charging device by use of a specialized alignment application, in accordance with some embodiments.

As shown in FIG. 13, the external user device initiates a fine-tuned charging device alignment procedure by selection on a user interface display 1300, which communicatively couples with the charging device. The user device includes an antenna that wirelessly communicates with an antenna in the charging device. Typically, the devices communicate by short-wavelength UHF radio waves, such as Bluetooth. The charging device and external user device establish secure communication by an authorization procedure or handshake, for example, by exchanging identifying information between the clinician programmer to ensure the charging device is communicating with an authorized device and ensure the information from the charging device is secure.

Figure 14:
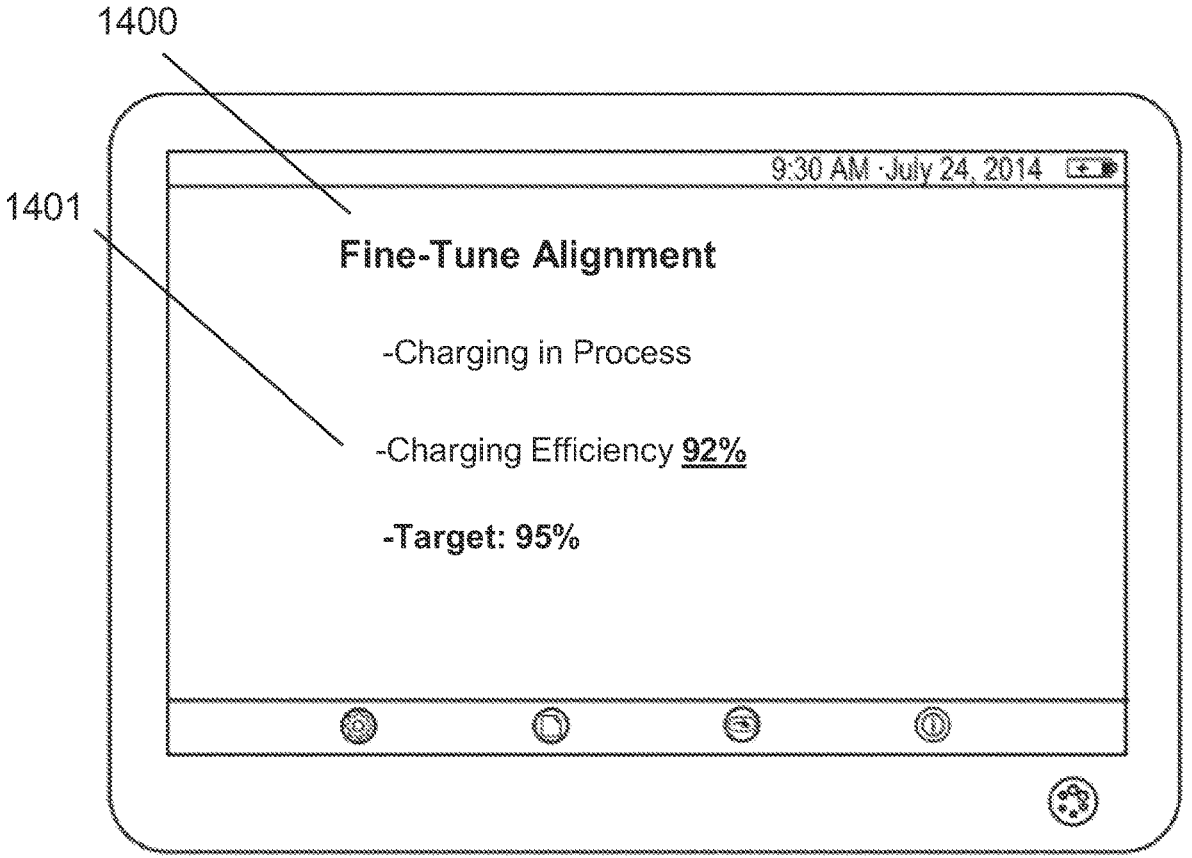

As shown in FIG. 14, the alignment procedure outputs a screen display 1400 for fine-tuned alignment that includes an alignment indicator 1401 on the graphical user interface display of the user device to facilitate fine-tuned alignment of the charging device during charging. As the charging device performs a charging operation, the interfaces displays the alignment indicator in real-time, which is constantly updated while the user manually adjusts the charging device to allow the user to determine the optimal position of the charging device. In this embodiment, the indicator 1401 is a dynamically updated display of charging efficiency. The charging efficiency may be determined from corresponding charging parameters already obtained by the charging device during charging. For example, the charging efficiency may be determined by comparing a power output of the charging device to the charging power generated in the implanted medical device. By observing the charging efficiency while manually adjusting the charging device through a range of suitable positions during which charging occurs, alignment between the coils of the charging device and the implanted device may be fine-tuned to locate the optimal charging position. Once the optimal position is found, its location may be noted by the user, by notes of the clinician made in the clinician programmer and/or by a photo taken by the clinician programmer and stored on the user device and subsequently communicated to the clinician and the patient. The optimal position information may be stored by the user device and associated with the patient, so that the patient or clinician can access the optimal position information at a later date so that the patient can continue to replicate this optimal position during subsequent charging session.

Figure 15:
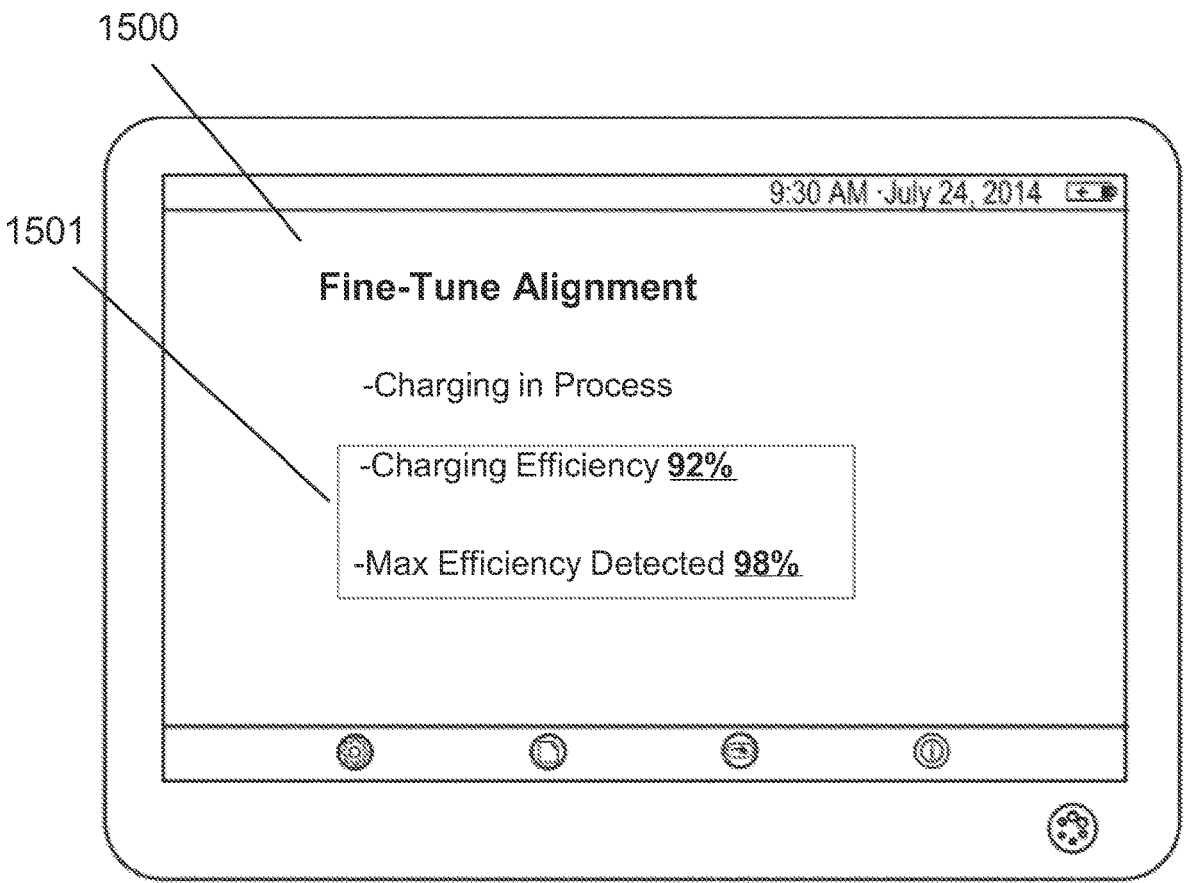
Figure 16:
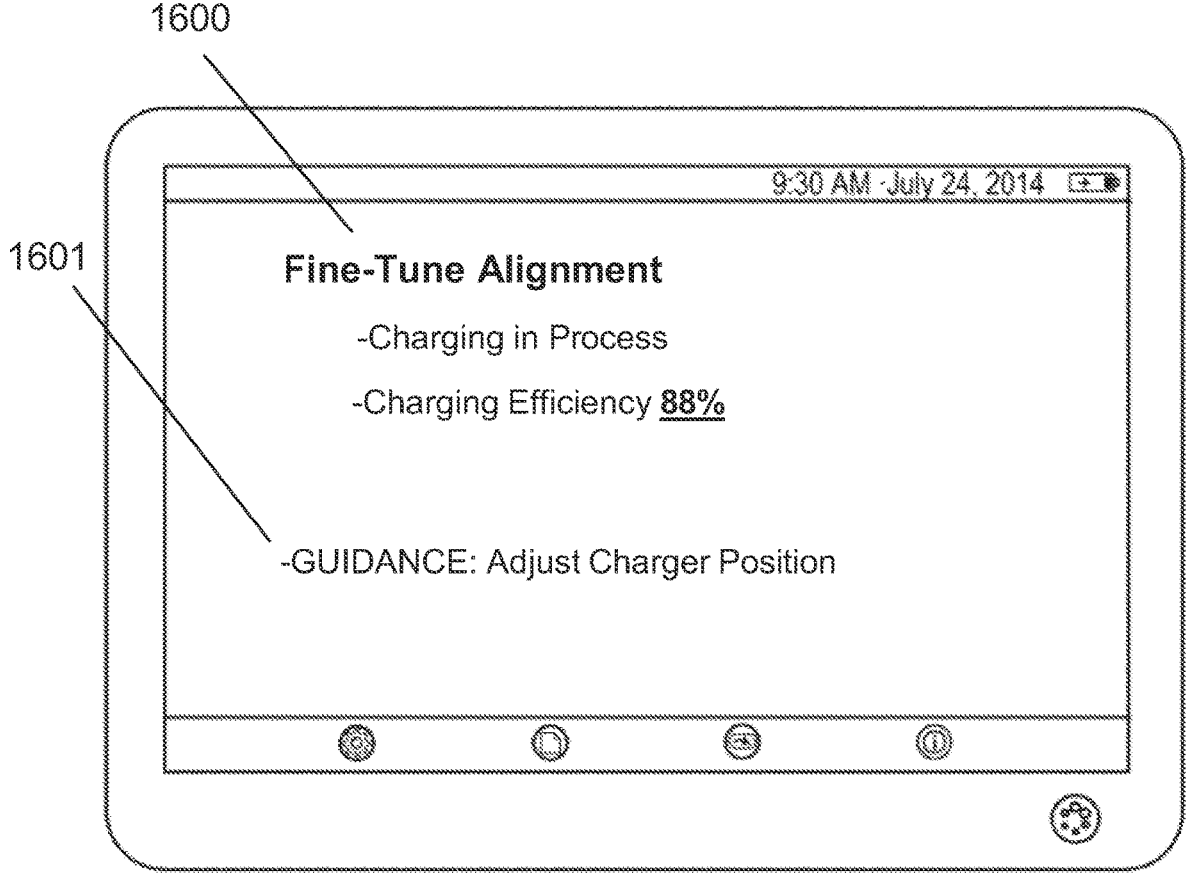

As shown in FIG. 15, the external user device display 1500 with alignment indicator 1501 can also display the maximum or peak charging efficiency detected during the alignment procedure so that the clinician and patient can readily identify when the optimal position is reached. This information may be communicated by various other means, for example, by a specialized charging metric unique to the neurostimulation system, a simplified rating system (Levels 1 through 5) that rates charging efficiency, or by audio alerts (e.g., instructions, beeps, tones), or any suitable means. In some embodiments, the indicator 1501 can include an additional indication (e.g., alert, beep, tone) when the current charging efficiency is at the maximum or target charging efficiency detected. In some embodiments, the external user device is configured (e.g., via the specialized application) to determine a target value and/or range for the alignment indicator. The value may be one or more charging parameters, a relationship between parameters (e.g., efficiency), or a quantitative measure (e.g., ranking, scale, etc.) In some embodiments, this target value and/or range is determined a function of any of the history of alignment indicator values; the history of one or more charging parameters; and an associated charging metric. In some embodiments, the history used for determining the target value and/or range is from a given charging session. In other embodiments, the history is from multiple sessions (e.g., 2 or more sessions, a set number of most recent sessions (e.g., 3, 4, 5), all charging sessions over a selected period of time (e.g., weeks, months, years), or all prior charging session. In some embodiments, the target range is less than a total range of values determined in a charging session. In some embodiments, the software application on the user device is configured to compile and/or analyze historical data of alignment indicators from multiple charging sessions and output the history of alignment indicators as a chart or other visual to the user, and/or determine trends on changes in alignment and charging parameters. This may be utilized to identify changes in position of the implanted medical device over time or changes in device performance necessitating intervention by the clinician, provider or device manufacturer. As shown in FIG. 16, the external user device display 1600 with alignment indicator can further include instructions or guidance 1601 to the user to further facilitate fine-tuned alignment. For example, if the current charging efficiency indicates that charging is suboptimal, the guidance can instruct the user to further adjust the charger position.

Figure 17:
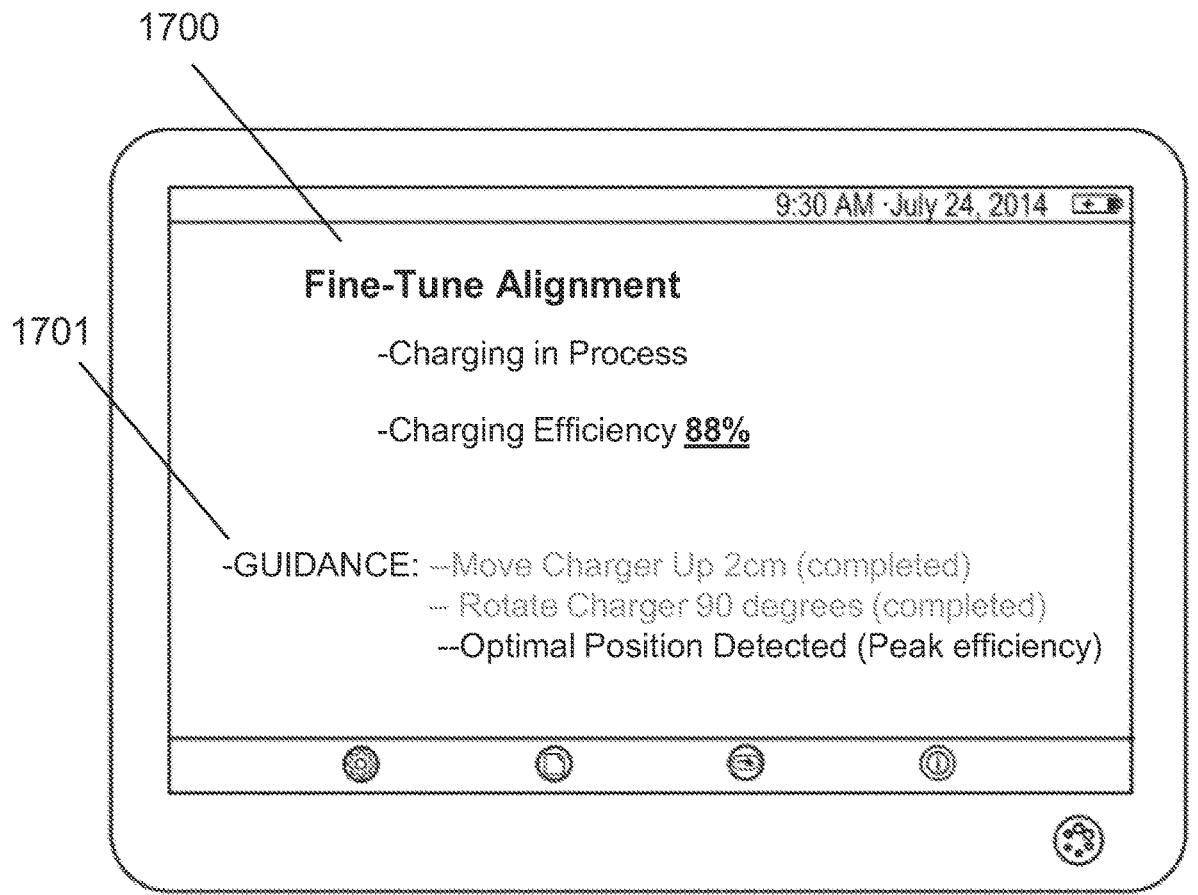

As shown in FIG. 17, the external user device display 1700 with alignment indicator can further include directional instructions or guidance 1701. The directional guidance can include specific instructions as to how the charging device should be adjusted, for example, instructions to move the charging device up/down/left/right by a suggested distance, or by rotating the charging device. This guidance may be informed by a positional sensor disposed on the charging device, such as one or more accelerometers, as described herein. The guidance can then indicate to the user when the optimal position is detected.

Figure 18:
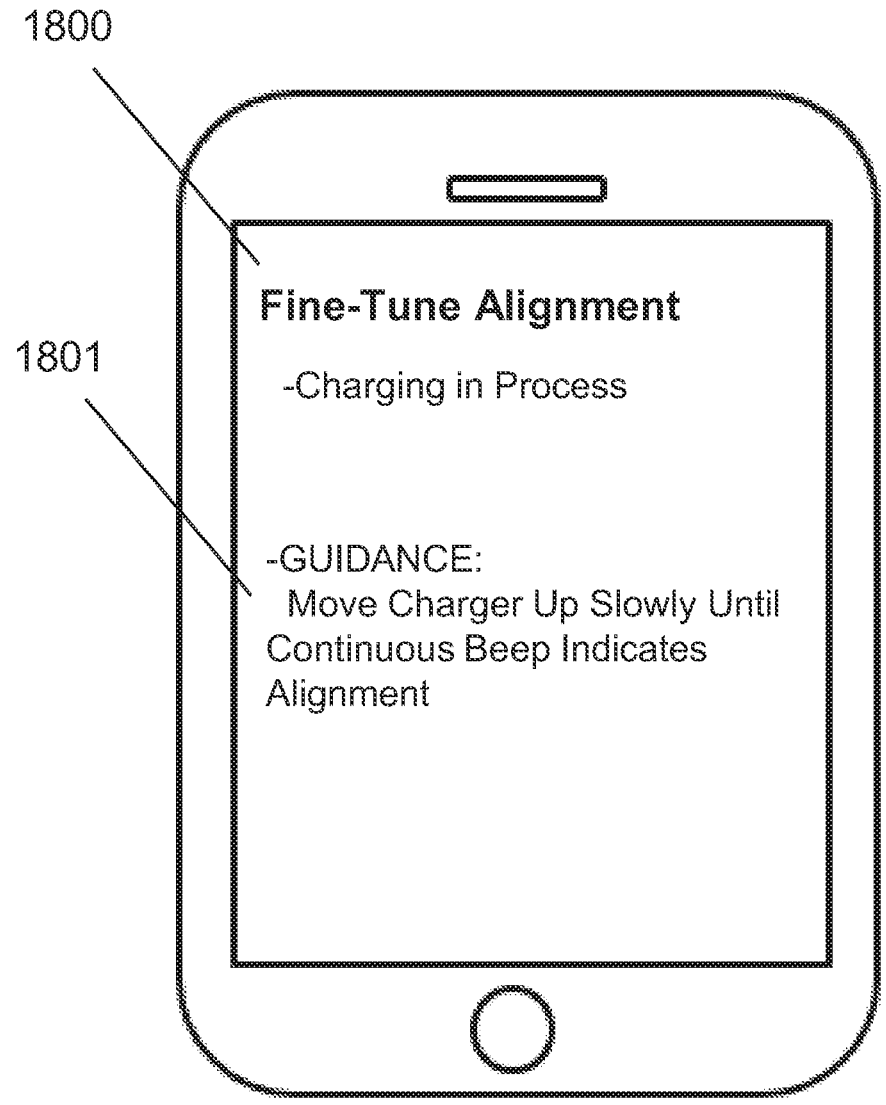

As shown in FIG. 18, the fine-tuned alignment procedure may be performed on a compact user device (e.g., smartphone) 1800 of the patient, specialist or clinician and can include any of the features of the alignment procedure described herein. In this embodiment, the alignment indicator includes directional guidance 1801, which may be provided in conjunction with an audio alert. For example, audio instructions for the user to move the charging device (e.g., move device left/right/up/down slowly or by an estimated distance). In some embodiments, the alert can change during adjustment of the charging device so that the user can identify when the optimal position is reached, for example, beeping that increases as charging efficiency increases and changes to a continuous beep when the maximum efficiency is detected.

This approach has the advantages of allowing the user to fine-tune charging device placement in a home setting as needed. In some embodiments, the patient can perform fine-tuned charging by use of the specialized application on their own personal device. In other embodiments, the patient's device can communicate with both the charging device and the specialist device or the clinician programmer through a network such that the specialist or clinician can facilitate fine-tuned adjustment remotely through the patient's device. In some embodiments, the fine-tuned alignment procedure may be automatically, at least partly, initiated when charging becomes deficient. For example, if routine charging becomes increasingly deficient, for example, as a patient loses weight, the patient's personal computing device (e.g., smartphone, tablet) can initiate a suggestion or alert to the patient to perform the fine-tuned alignment of the charging device and either lead the patient through the procedure on their personal computing device, or facilitate the procedure being performed remotely by the specialist, clinician or health care provider utilizing the user's personal computing device communicating with the clinician's computing device through a remote server or network.

Figure 19:
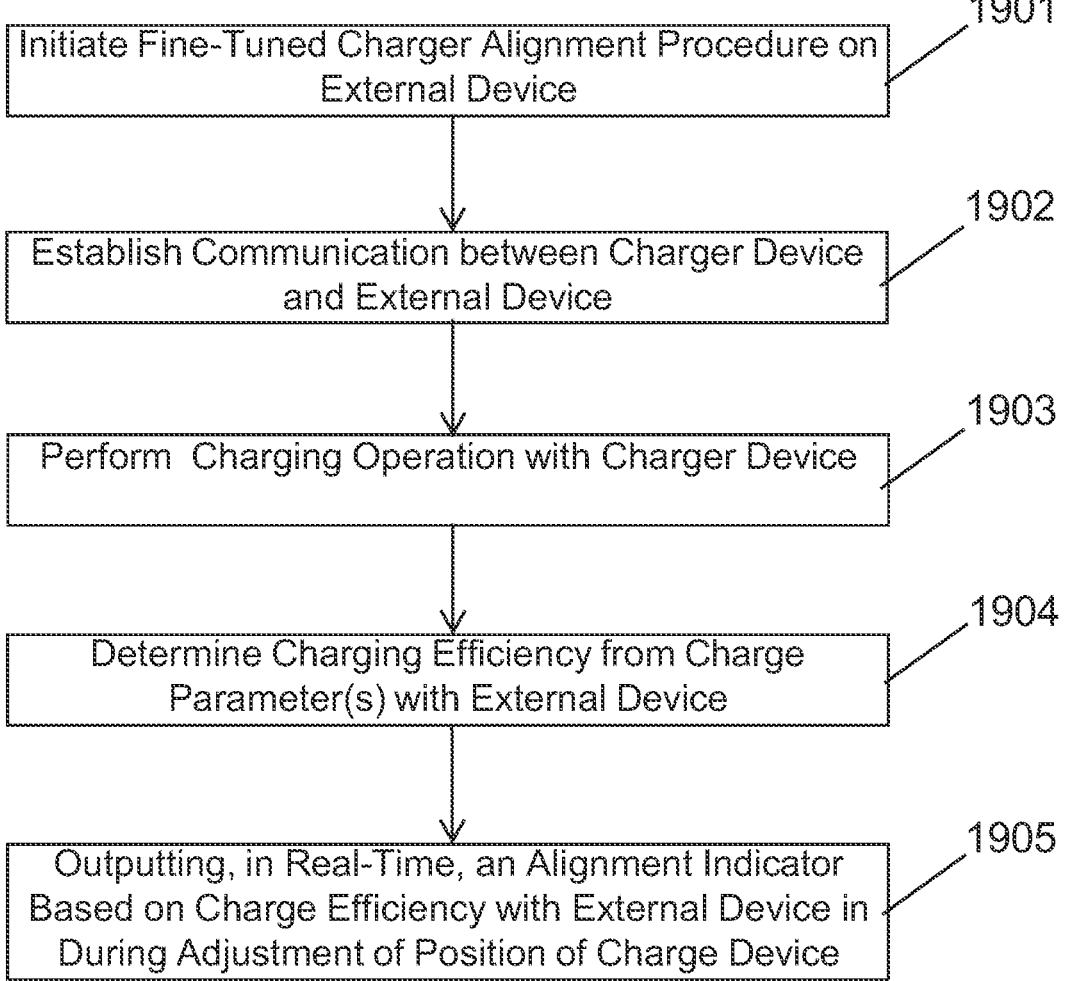
FIG. 19-20 shows exemplary methods of charging an implanted device with a charging device and an alignment indicator, in accordance with some embodiments.
Figure 20:
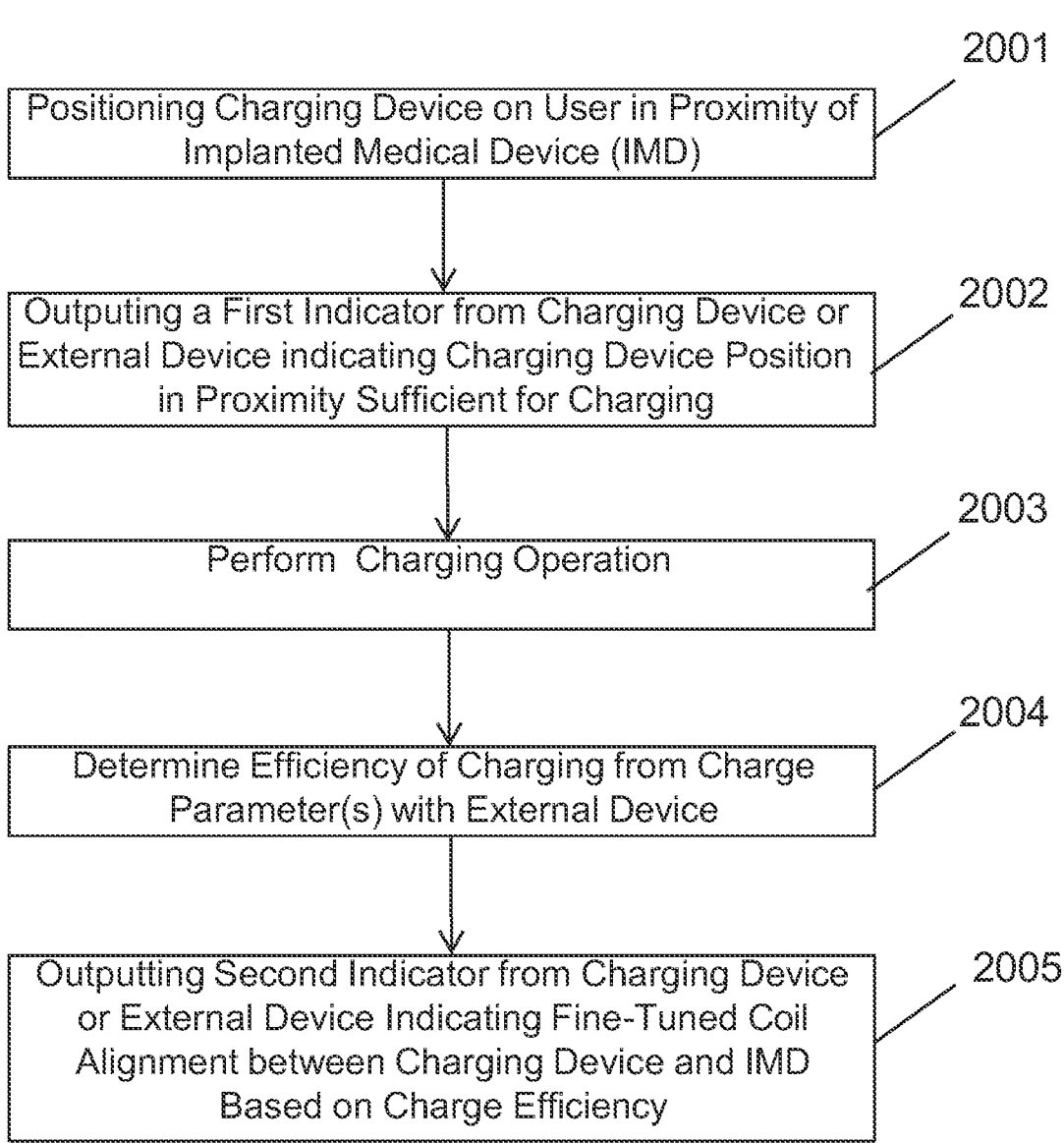

FIG. 19-20 shows exemplary methods of charging an implanted device with a charging device and an alignment indicator, in accordance with some embodiments.

As shown in FIG. 19, the method can include steps of: initiating the fine-tuned charger alignment procedure on an external device 1901; establishing communication between charger device and external device 1902; performing charging operation with the charger device 1903 and communicating one or more charge parameters to the external device; determining charging efficiency from charge parameter(s) with the external device 1904; and outputting, in real-time, an alignment indicator based on the charge efficiency with external device during adjustment of the position of the charging device 1905. The alignment indicator can include one or more of the features described herein, or in combination (e.g., visual, audio, haptic).

As shown in FIG. 20, such methods can include steps of: positioning a charging device on user in proximity of implanted medical device (IMD) 2001; outputting a first indicator from charging device or external device indicating charging device position in proximity sufficient for charging 2002; performing a charging operation; determining efficiency of charging from charge parameter(s) with external device or charging device 2004; and outputting second indicator from charging device or external device indicating fine-tuned coil alignment between charging device and IMD based on charge efficiency 2005. The alignment indicator can include one or more features described herein, or in combination (e.g., visual/audio/haptic).

In another aspect, functionality of the charging device in regard to any of the alignment indicator features herein may be affected by a software push through an external user device in communication with the charging device, for example, the specialist device, clinician programmer or the patient's personal computing device (e.g., smartphone). In some embodiments, the specialized software configured for fine-tuned alignment can facilitate the software push through the clinician programmer or the patient's personal computing device to the charging device. In some embodiments, the specialized software application may be configured to upgrade the software on the implanted medical device (e.g., IPG) through the charging device from the user device while the charging device is positioned on the patient's body over the IPG (e.g. immediately prior, during or after charging). The upgrade can include features pertaining to charge alignment and/or various other features unrelated to charging alignment. In another aspect, the periodic communication between the user device and the charging device during charging sessions may be utilized for various auxiliary functions, including programming of stimulus profiles from the user device (e.g., by the clinician or sent by the clinician to the patient's user device) and/or downloading data logs from the implanted device.

In one aspect, the charger alignment features described herein are incorporated into a specialized software application (e.g., SmartCharge App) that is operable on a computing device of a specialist, the clinician or the patient to facilitate improved alignment of the corresponding charging coils of the charging device and the implanted medical device. In some embodiments, the alignment application is deployed on a device associated with a specialist (e.g., field technician, device provider representative, or clinician specialist). In some embodiments, the application is provided on a patient device to aid the patient in improving alignment of the charging device with the implanted medical device. In some embodiments, the user connects the external user device (e.g., smartphone/tablet/laptop) to the charging device for local communication (e.g., by Bluetooth) and monitors the charge data and efficiency between the charging device and the implanted medical device using the specialized software application.

In some embodiments, the charger alignment tool is a specialized application (e.g., SmartCharge App) that is separate from the standard, routine charging application used by the patient during routine charging. In some embodiments, the specialized alignment application is configured solely for use by a specialist. Accordingly, this specialized charger alignment application can utilize a special login to ensure proper authorization and authentication of the respective devices. A flowchart of a login protocol is shown in FIG. 21 and an exemplary login screen is shown in FIG. 22.

Figure 21:
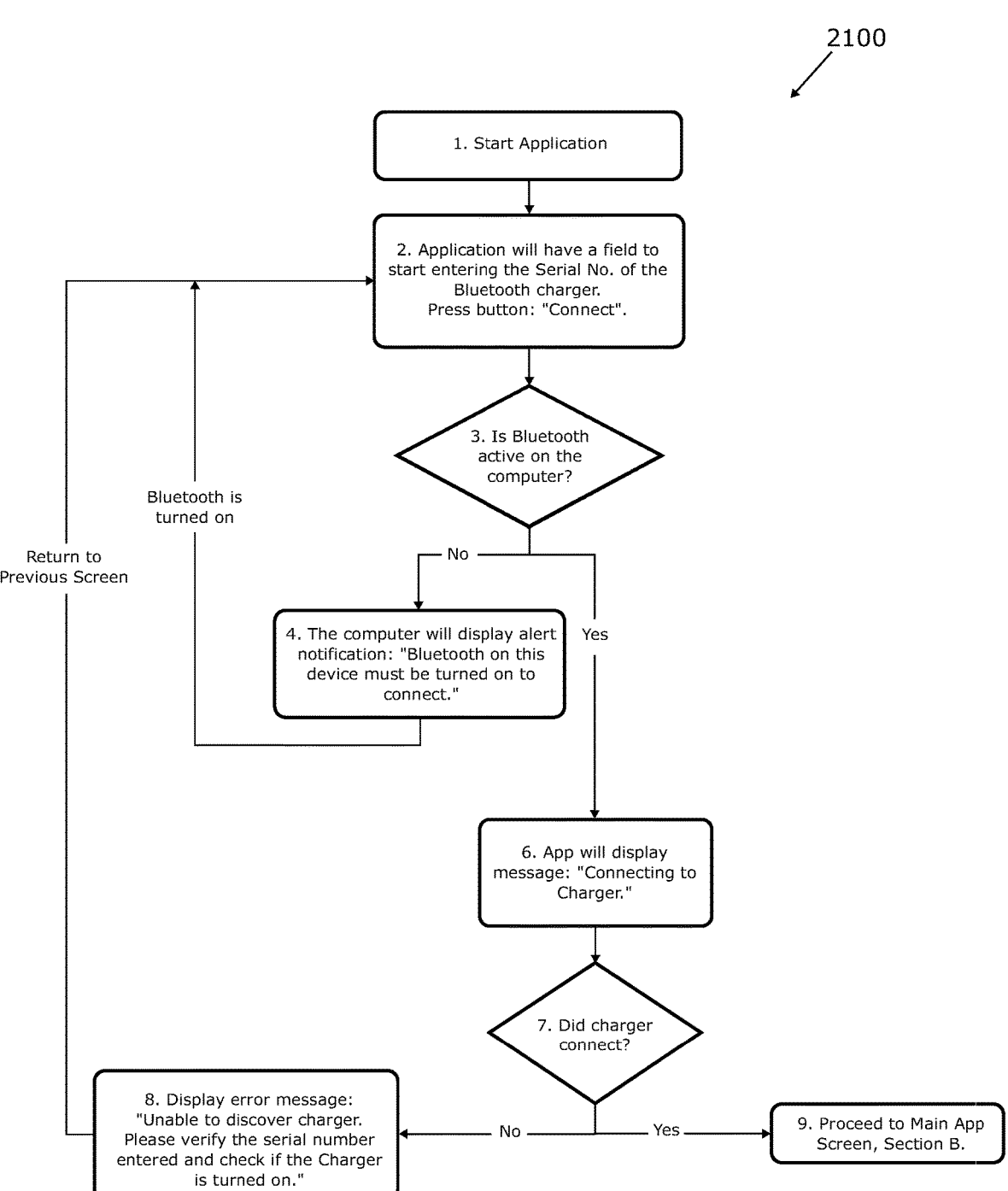
FIG. 21 shows a flowchart demonstrating use of a charger alignment tool, in accordance with some embodiments.

FIG. 21 shows an exemplary login flowchart decision tree embodied in the programmable instructions of the software applications stored on the user device. The flowcharts include step (1) starting the application, and then step (2) displaying login screen (see for example, FIG. 22) through which identifying information (e.g., serial number of the charger device) is entered via a user interface of the user device before initiating a wireless connection (e.g., by Bluetooth) by pressing of a "Connect" button. Next, the software application performs step (3) assessing whether wireless communication (e.g., Bluetooth) is active on the user device. If not active, then step (4) notifies the user that wireless communication must be turned on and returns to step (2); if active, then the program performs step (6) wirelessly connecting user device to charger device and displaying action indicator (e.g., "Connecting to Charger"). Next, the software application performs step (7) assessing whether charger device connected to user device. If not connected, the software application displays an error message on the user device (e.g., "Unable to discover charger. Please verify the serial number entered and check if the Charger is turned on"). If connected, the software application performs step (9) which proceeds to the main display screen to perform charging alignment (see screens in FIGS. 23-24).

Figure 22:
FIG. 22-24 shows exemplary user display screens with charging alignment indicators shown during charging, in accordance with some embodiments.

FIG. 22 shows a login screen 2200 of the charger alignment tool application on the user device. This screen displays login instructions to the user to initiate charger alignment as described herein. These instructions to the user include: 1) ensuring the user device includes wireless communication (e.g., Bluetooth) activated, 2) ensuring the charger device is "on", and 3) entering identifying information (e.g., serial number of the charger device). In some embodiments, this last step provides error-proofing by obtaining a 10-digit serial number from the back of the charging device. This ensures secure connection to the appropriate device. The login then provides a button by which the user can wirelessly connect the user device to the charging device. In some embodiments, this login screen is compatible with a conventional touch-screen interface of a specialized smart-phone or tablet device, in other embodiments, the software application may be used on a standard personal device (e.g., smartphone/tablet).

Figure 23:
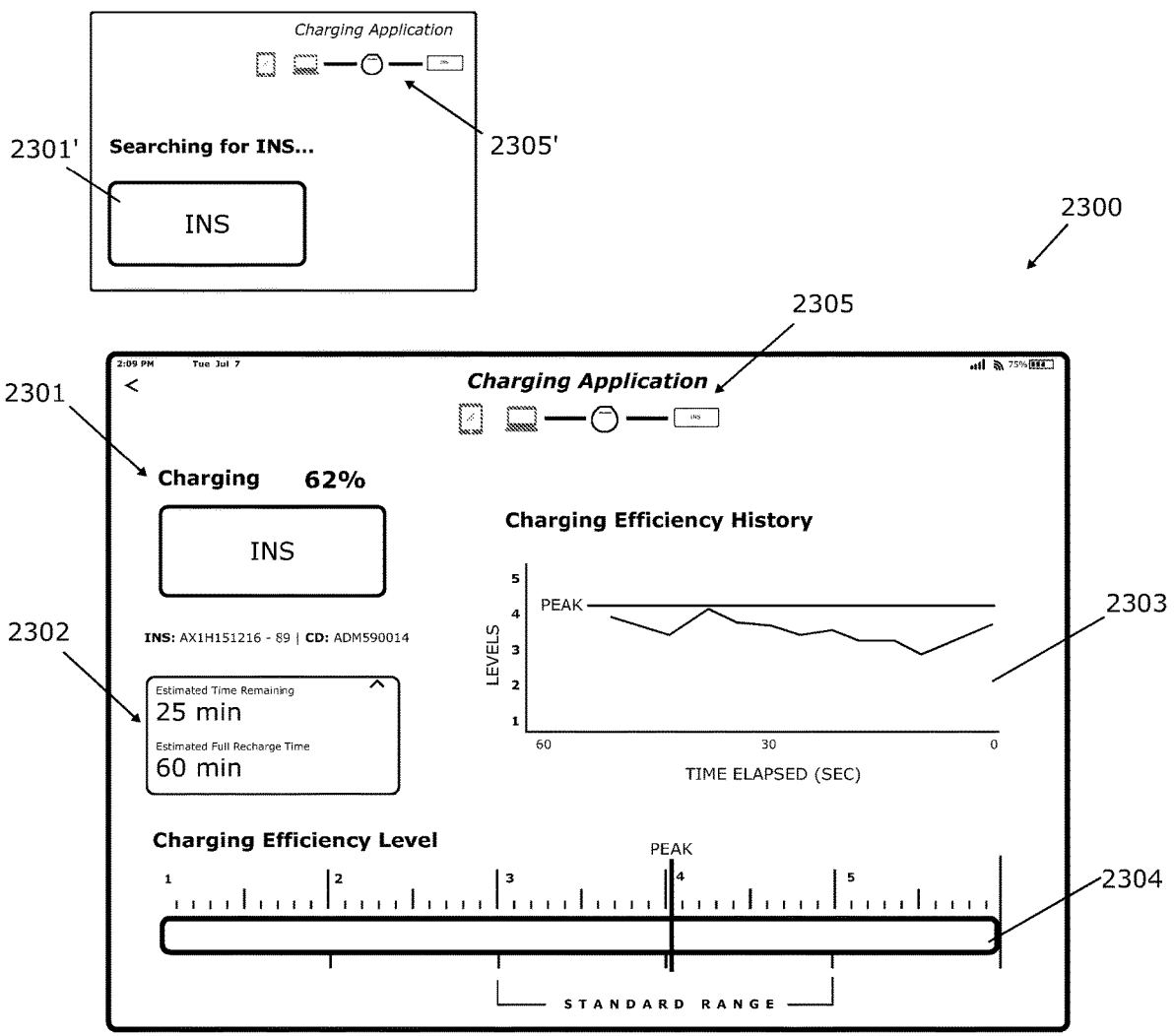

FIG. 23 shows an exemplary main screen 2300 of the specialized alignment application (e.g., "SmartCharge") for facilitating fine-tuned charging alignment. This main screen displays various indicators pertaining to the status of the batter, connection and charging so as to allow for fine-tuned alignment of charging coils based on the one or more charging parameters obtained from the charging device. On the main display, the back button (e.g., left arrow) at the top left takes the user back to the charger login screen in FIG. 22, which will disconnect the charger device from the user device until the "Connect" button is pushed again. Below the back button, is a battery/charging status indicator 2301, which shows the status as "Charging" and battery capacity as 62%. At the top of the main screen is a connectivity indicator 2305, which shows a green circle indicating that the user device and implanted neurostimulation system (INS) is communicatively coupled. If the INS loses connectivity with the user device, then the main screen would show status indicator 2031' (see upper left detail displaying "Searching for INS . . . ") and connectivity indicator 2035' would show as gray bars indicating no connection. The main screen further includes a charging time indicator 2302 indicating time parameters of charging. This indicator may be included in a collapsible menu entitled "Estimated Time." Typically, the estimated time remaining is refreshed periodically, (e.g., every 30 seconds, every minute). The main screen further includes a historical charging efficiency indicator 2303, shown at right, which shows a history or log of the charging efficiency over a period of time during the charging period. The charging efficiency history is typically shown as a graph but can also be shown as a series of bars. The main screen further includes a current charging efficiency level indicator 2304, shown at bottom, which shows the current real-time charging efficiency, and may further show the standard charging range and peak. Once the INS is fully charged, the top left header will read "Fully Charged" and a pop-up notification will appear that states: "This INS is fully charged. Session has ended. To use SmartCharge with this INS, please wait for a decrease in charge below 90%."

In one aspect, the historical charging efficiency indicator 2303 can indicate variations in charging efficiency over an elapsed period of time during charging. In the embodiment in FIG. 23, the period of time is a 60 second period. The graph is continually updated to reflect the most recent period of time elapsed, thereby allowing the user to observe variations during charging as the charging device is actively moved. In this embodiment, the graph is a bar that animates to the right where the right-most value is the most recent charge level. Peak efficiency may be marked on the graph with a straight horizontal line across the graph, which shows the highest achieved efficiency of the charging session.

Figure 24:
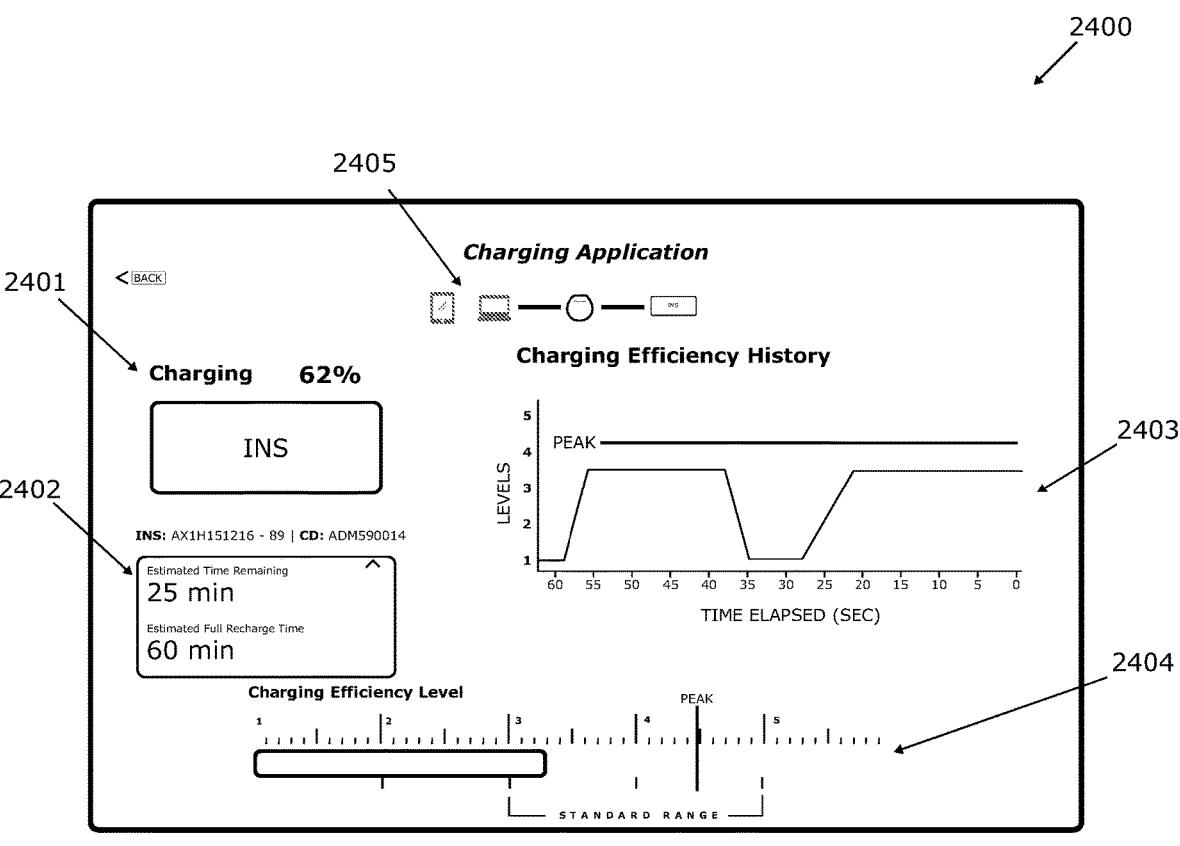

FIG. 24 shows an alternative main screen 2400 of the specialized charge alignment software application. Similar to that in FIG. 23, the main screen shows the connection status indicator 2405, the charge/battery status indicator 2401, the charging time indicator 2402 (drop down menu title shown), the charging efficiency history indicator 2403, and a current real-time charging efficiency level indicator 2404 with standard range and peak level indicator, as shown. FIGS. 25-27 show detail views of select indicators as well as additional charging level indicator based on percentage charged and rotational alignment.

FIG. 25 shows a charging time indicator 2502 indicating time parameters of estimated time remaining and estimated full recharge time. In this embodiment, the indicator is shown within a collapsible menu. In some embodiments, the estimate time remaining is determined based on an average steady state charge rate and the initial battery capacity at the onset of the charging session. In some embodiments, the initial battery capacity is determined based on a voltage measurement of the battery obtained by the user device from the charging device. The software application determines the total estimated time to perform a full charge, and the estimated charging time remaining, which is continually updated.

FIG. 26 shows a charging efficiency indicator 2601. In this embodiment, the levels are indicated in contrasting colors (e.g., green vs. gray) depending on the percentages. Typically, the targeted efficiencies are levels 3-5 (shown in green), to contrast with the lower less optimal efficiency levels 1 and 2 (shown in gray). FIG. 17 shows a rotational charging efficiency indicator 2701 that shows the charging efficiency levels associated with each rotational alignment. Typically, this indicator is observed while the charging device remains at one position and is rotated by the user so as to facilitate optimal rotational alignment conditions between the INS and the charging device. In this embodiment, the rotational alignment may be in reference position (e.g., initial position) and be determined relative the reference (e.g., angle of rotation in clockwise direction).

FIG. 28 shows a detail view of the current charging efficiency level indicator 2800, which shows the current charging efficiency level as a bar, for example an animated bar representing charging efficiency determined in real-time. The bar can extend between the differing charging efficiency levels 1 through 6. A standard range 2802 of typical charging efficiencies may be indicate the expected efficiency and to guide the clinician and/or patient during positioning. The bar graph can further include a peak level indicator 2803 (e.g., vertical bar), which indicates the highest charging level determined during the charging session.

In another aspect, the charging alignment tool and associated software application may be specially configured for use by a specialist (e.g., field technician, representative of a device provider, clinician specialist). For example, the software application described herein may be provided with specialist-only login access for use on a user device of the specialist for patient training purposes and/or to troubleshoot charging alignment issues experienced by certain patients. In some embodiments, the specialized alignment application is configured for use with a specialized charging device having advanced charging functionality to streamline the charging alignment procedure.

In some embodiments, the alignment application provides the specialist (e.g., field technician, sales field team member, device provider representative, clinical specialist) with real-time feedback on the quality of the alignment between the charger device and the INS in order to optimize patient charging through high quality patient education and training, or to allow advanced troubleshooting, including when the INS is in a sleep mode or hibernation. This approach of including the alignment tool features only on a specialist device improves the patient experience while minimizing the occurrence of unnecessary devices revisions and updates on the standard devices and applications used by the clinician and patients.

Figure 29:
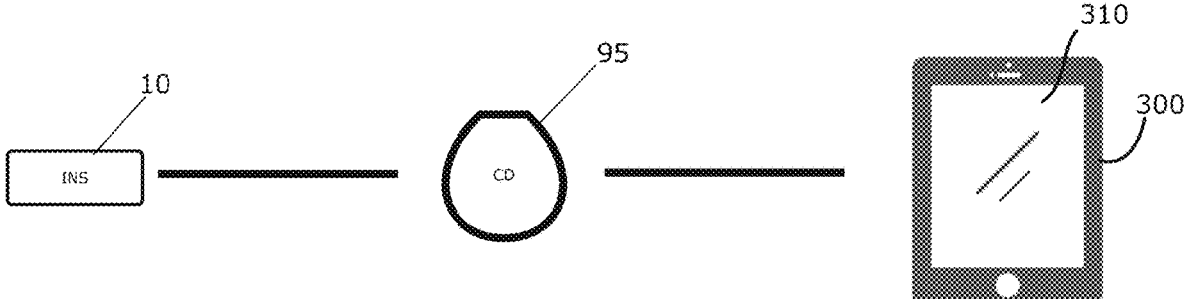
FIG. 29 shows an exemplary charging alignment tool that includes a specialist's user device having a charger alignment application thereon that communicates with a specialized charging device that charges an implantable medical device, in accordance with some embodiments.

In one aspect, the charge alignment setup can utilize a specialized charging device with additional functionality as compared to a standard charging device. FIG. 29 shows a system utilizing a specialist's device 300 with display 310 and a specialized charging device 95 (e.g., "Green Charger") operable to communicate the charging parameters to the device 300 so as to display the alignment indicator on the display 310. In such embodiments, the specialized chargers can include additional communication functionality (e.g., Bluetooth enabled) so as to communicate with the user device (e.g., user device of the specialist), whereas the standard charging device for most patients does not require this feature. Similarly, the software application may be configured to be operable only on a user device accessed by the specialist. In some embodiments, the software application is configured to display at least battery status information and a charging efficiency indicator of the charging connection between the charger and INS. The display can further include time parameters of charging or charging efficiency history, as described above.

Figure 30:
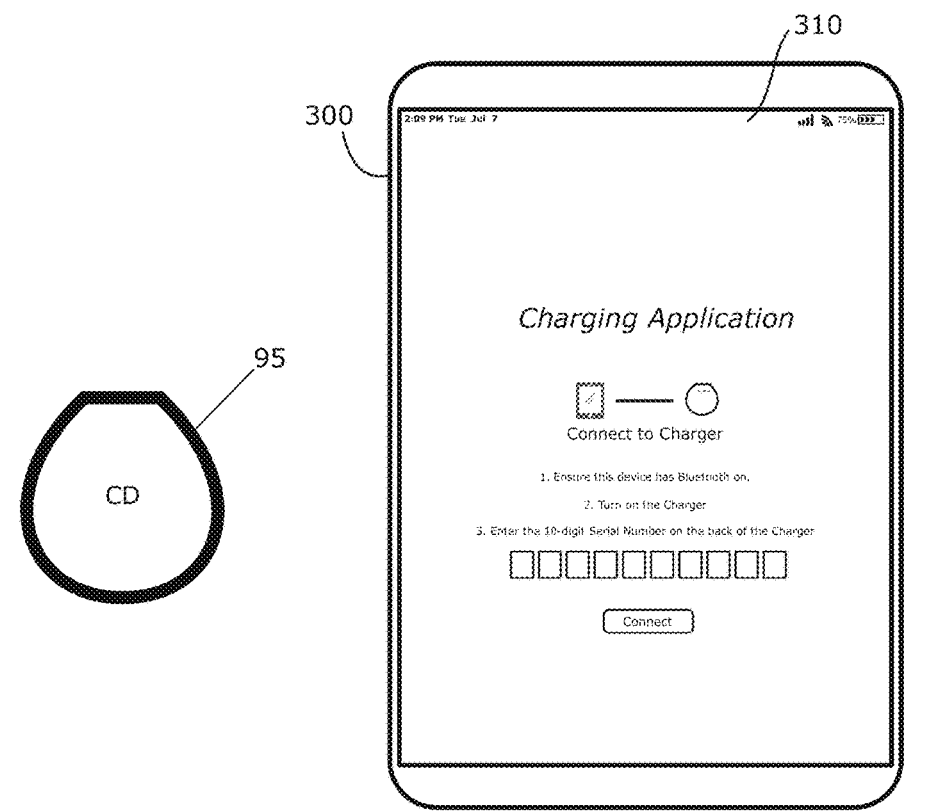
FIG. 30 shows an initial login of the charger alignment application to connect the specialist's user device to the specialized charging device, in accordance with some embodiments.

FIG. 30 shows the specialized charging device 95 being connected to the specialized software application on specialist's user device 310. The user display 310 shows the initial login screen, similar to that in FIG. 22, to facilitate initial connection with the specialized charging device. In some embodiments, if the INS battery is depleted and in hibernate mode, some charging will be required before the specialized application can communicate with the INS.

After connection, the charging device may be used in the usual manner to commence wireless recharging of the INS. The specialized application communicates by local communication (e.g., Bluetooth) with the specialized charging device to obtain or more charge parameters to determine and display the charging efficiency level, which may be used to determine a more efficient charging position of the charging device on the patient. More efficient charging means faster charging with fewer disconnections. Charging efficiency depends on: INS depth, charger alignment and charger rotation.

Figure 31:
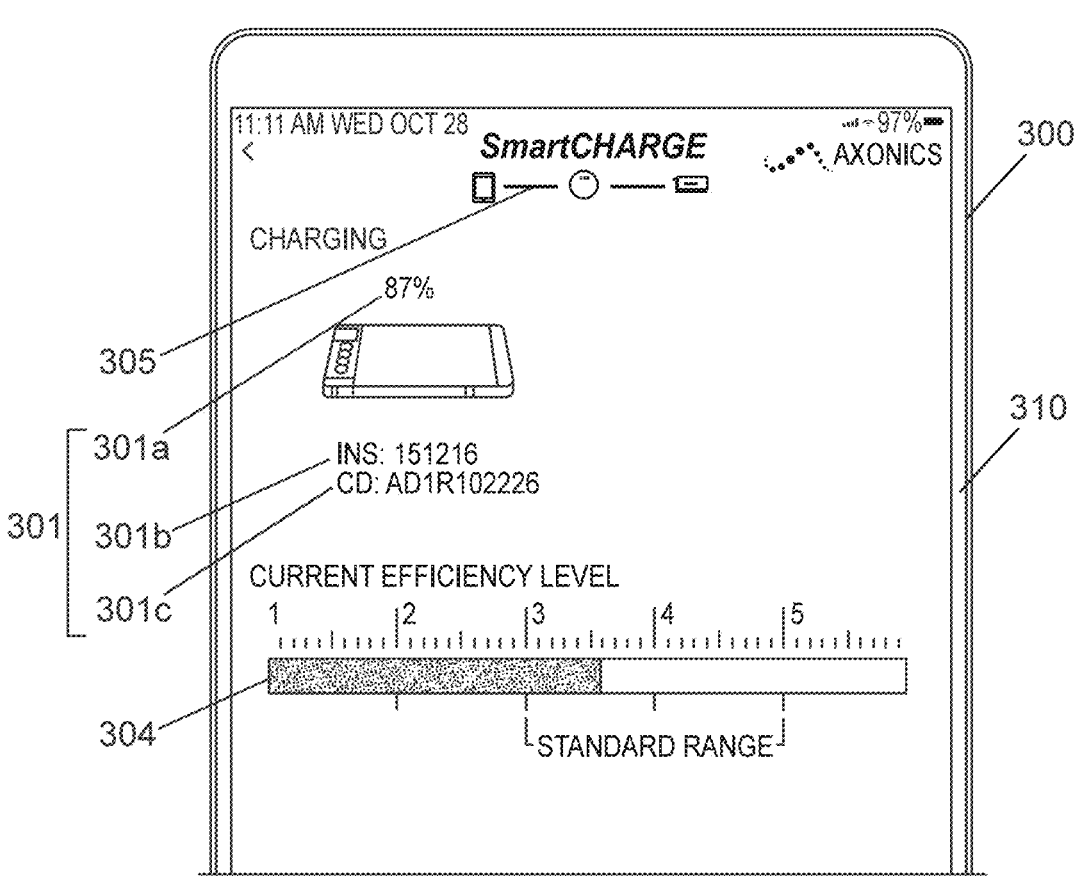
FIG. 31 shows a main display screen of the specialist's user device displaying various charge information indicators thereon for assessing charger alignment, in accordance with some embodiments.
Figure 32:
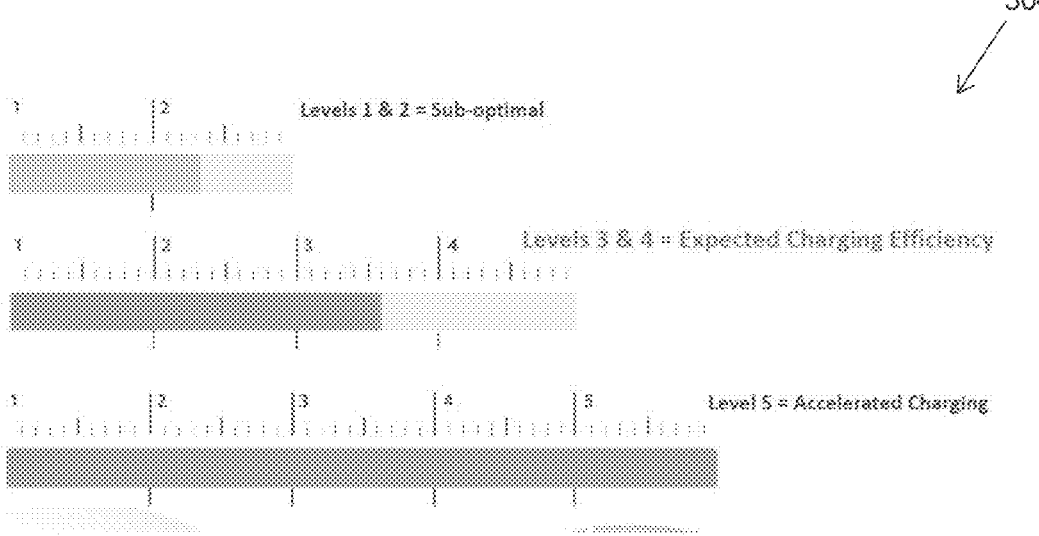
FIG. 32 shows the differing levels of an exemplary charging efficiency indicator, in accordance with some embodiments.

During charging, the alignment application displays the main screen (see FIGS. 23-24) on display 310 of specialist device 300 shows various indicators relating to charging. In the embodiment shown in FIG. 31, the application is configured to show the battery/charging status indicator 301, current efficiency level indicator 304, and the connection status 305. The battery/charging status indicator 301 can show the battery/charge status 301*a* (e.g., 87%) and charging status (e.g., "Charging"), the INS serial number 301b and the charging device serial number 301c. As shown in FIG. 32, the current efficiency level indicator 304 (as described with respect to FIGS. 23-24) can extend across five charging levels from lowest to highest. Levels 1 and 2 correspond to sub-optimal charging levels, where first-order alignment is sufficient for charging, but second-order alignment results in poor charging efficiency. Levels 3 and 4 correspond to optimized charging where the second-order alignment is improved resulting in increased charging efficiency. Most patients charge at Level 3 and 4 efficiencies within the "standard range", and will achieve expected charging times. In some embodiments, the system may be configured with a Level 5 corresponding to an accelerated charging. The specialized charging device may be specially configured with an accelerated charging mode that can charge faster than the standard mode of the standard charging device used by patients. Level 5, accelerate charging, may not be achievable or necessary for all patients. This mode may allow for even further enhanced visibility of the optimal alignment position. In some embodiments, this accelerated charging feature enables the charging device to charge and wake up the hibernated INS more quickly. In some embodiments, after the INS is charged sufficiently to establish a connection, the specialized charger charges at the same rate as a standard charged used by the patient.

Figure 33:
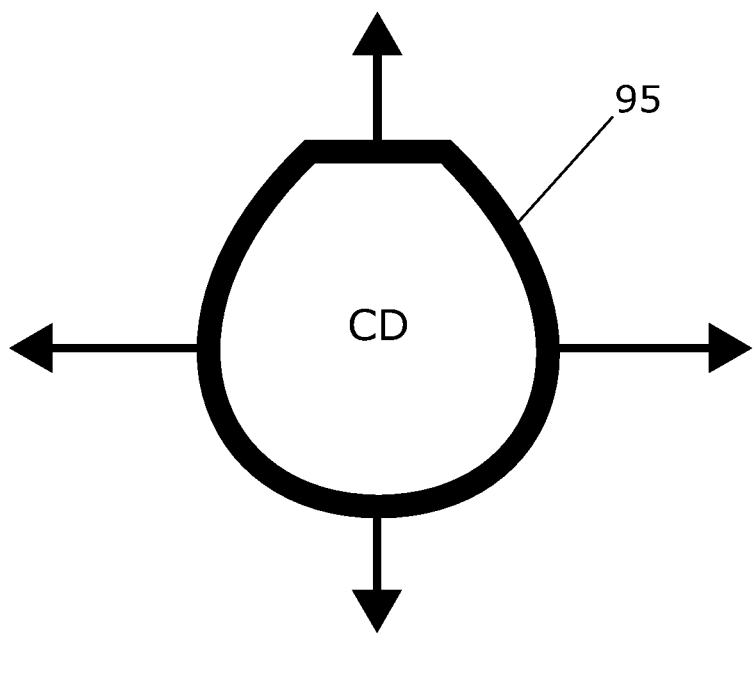
FIGS. 33 and 34 show the manner in which the charging device is moved during charging while using the charger alignment feature to assess charging alignment, in accordance with some embodiments.
Figure 34:
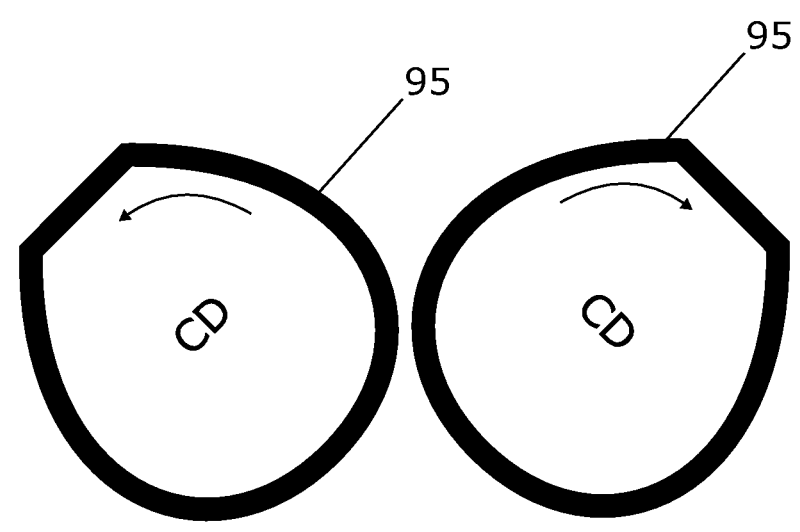

While the charging status/efficiency indicators are shown to the specialist on the main screen of the user device, the user moves the charging device as shown in FIGS. 33 and 34. The instructions below may be provided via the specialized app or by instruction materials provided with the specialized application and/or specialized charger. FIG. 33 shows the user moving the charger slowly up, down, medial or lateral to ensure the charger is optionally aligned over the INS. FIG. 34 shows the user rotating the charging device 95 counterclockwise (at left) or clockwise (at right). In some embodiments, the user can roughly determine the angle by observing the position of a feature of the charging device (e.g., logo, marker, flattened top portion). The target orientation may be rotated relative a reference (e.g., vertical or horizontal axis, or an incision of INS implantation). A patient can manually feel the flattened top portion when holding the charging device to achieve a particular rotational orientation, or the patient can position the charging device in the desired rotational orientation within a belt before attaching. Preferably, the belt is configured to allow the patient to rotate the charging device while secured within an opening of the belt.

In an exemplary alignment procedure, the user moves the charging device during charging (e.g., as in FIG. 33) while observing the variation in real-time charging efficiency level. During this variation, the peak level is indicated by the application. Once the charging efficiency is maintained near or at peak level, the user maintains and notes that position on the patient. This position may be noted relative the incision of the INS implantation. Optionally, the user then rotates the charging device and observes any variation in charging efficiency to determine the optimal rotational orientation to provide best charging efficiency. This rotational orientation is also noted. In some embodiments, palpating the INS may provide a better understanding of the required charging device alignment before the procedure, which can then by verified with the specialized application.

Once the optimal charging position is determined by the specialist, it is recommended that the specialist 1) make sure the position is repeatable in an attachment device (e.g., adhesive device, or belt), 2) take a picture or detailed note or drawing as to the ideal position, and 3) have the patient practice the ideal placement. In one aspect, this software assisted procedure may be used during initial post-operative charging training so as to start the patient out with the best charger placement and charging experience. In another aspect, this procedure can also be used for troubleshooting in patients experiencing sub-optimal charging. In some patients, where this procedure indicates that optimal charging may be difficult to achieve, charging still occurs at Levels 1 and 2. For such patients that cannot achieve charging at Level 3 or higher, the specialist may suggest charging more frequently or using lower therapy setting where possible to prolong battery life.

FIG. 35 shows an exemplary method of assessing alignment by a specialist, which may be used for initial training and/or troubleshooting of charging alignment. The method includes steps of: establishing communication between a user device and an external charging device, wherein the charging device is configured for transcutaneously charging of an implanted medical device and the user device is an external computing device associated with a specialist and having a specialized application thereon for assessing charging alignment 3501; charging the implantable medical device with the external charger when at least a first-order alignment is achieved 3502; receiving, with the user device, one or more charging parameters or an associated charging metric from the charging device during transcutaneous charging of the implanted medical device 3503; displaying on a display of the user device with the specialized application, a real-time charging efficiency indicator based on the one or more charging parameters or metric, wherein the charging efficiency indicator corresponds to a fine-tuned alignment between the external charging device and the implanted medical device 3504; and moving the external charger device on the patient while the specialist observes variations in the charging efficiency indicator to determine an optimal position of the external charging device for charging 3505. In some embodiments, the specialized application may be configured for use only by the specialist. In some embodiments, the charging device may be a specialized device configured for use with the alignment application of the specialist's device and can further include additional charging functionality to streamline the alignment optimizing procedure.

In the foregoing specification, the subject matter is described with reference to specific embodiments thereof, but those skilled in the art will recognize that the subject matter is not limited thereto. As used herein "user device" can refer to a device of any of a patient, a clinician or a specialist associated with the device provider or manufacturer. Various features and aspects of the above-described subject matter may be used individually or jointly. Further, the subject matter may be utilized in any number of environments and applications beyond those described herein without departing from the broader spirit and scope of the specification. The specification and drawings are, accordingly, to be regarded as illustrative rather than restrictive. The terms "comprising," "including," and "having," as used herein, are specifically intended to be read as open-ended terms of art.

What is claimed is:

1. A system for facilitating alignment between an external charging device and an implantable medical device in a patient, the system comprising: an external charging device having a charging coil disposed within a housing and configured to magnetically couple with a corresponding receiving coil of the implantable medical device, wherein the external charging device includes an antenna configured for communicating with one or more external devices, and a processor configured to control charging with the charging coil and monitor one or more charging parameters during charging, wherein the external charging device comprises one or more indicators that are configured to indicate a first-order alignment of the external charging device with the implantable medical device and effect charging upon detection of the first-order alignment; and a portable user device, the portable user device having a housing, an antenna for communicating with at least one of the external charging device and the implantable medical device, a user interface, and a processor operably coupled to the antenna, the user interface and a memory having stored thereon a software application configured for at least one of training and troubleshooting of charging, wherein the software application includes executable instructions configured to: establish wireless communication with the external charging device; receive a wireless communication of the one or more charging parameters or an associated charging metric during charging; and display a charging efficiency indicator in real-time that corresponds to a fine-tuned alignment between the external charging device and the implantable medical device, wherein the charging efficiency indicator is based on the one or more charging parameters or the associated charging metric.

2. The system of claim 1, wherein the portable user device is configured for use by a specialist who is at least one of a field technician, a representative, and a clinical care specialist associated with a provider of the implantable medical device.

3. The system of claim 1, wherein the software application includes a secure logon to ensure secure connection between the portable user device and the external charging device.

4. The system of claim 1, wherein the portable user device is a tablet device.

5. The system of claim 1, wherein the external charging device is configured to communicate by a first type of communication with the implantable medical device and to communicate by a second type of communication with the portable user device.

6. The system of claim 5, wherein the first type of communication is MedRadio and the second type of communication is Bluetooth.

7. The system of claim 1, wherein external charging device is a specialized charging device configured for use with the software application.

8. The system of claim 7, wherein the external charging device is configured for use only by a specialist.

9. The system of claim 7, wherein the external charging device includes an accelerated charging mode that operates with increased charging parameters as compared to a standard charging mode of a standard charging device of the patient.

10. The system of claim 9, wherein the external charging device is configured to charge the implantable medical device in the accelerated charging mode when the implantable medical device is in a hibernation and/or a low battery state at least until communication may be established.

11. The system of claim 10, wherein the external charging device is further configured to charge the implantable medical device at a same rate as the standard charging mode after communication is established.

12. The system of claim 1, wherein the software application is configured to display the charging efficiency indicator on a main display screen that further displays one or more additional indicators.

13. The system of claim 12, wherein the charging efficiency indicator is a bar extending between multiple differing charging efficiency levels, wherein the bar dynamically updates to show a current charging efficiency level in real-time.

14. The system of claim 13, wherein the charging efficiency indicator further shows a peak level during a charging session.

15. The system of claim 14, wherein the one or more additional indicators include a charging efficiency history indicator.

16. The system of claim 14, wherein the one or more additional indicators further include a battery charge status.

17. The system of claim 14, wherein the one or more additional indicators further include a connection status.

18. The system of claim 14, wherein the one or more additional indicators further include a charging time indicator.

19. The system of claim 18, wherein the charging time indicator comprises one or both of an estimated charging time remaining and a total estimated charging time.

20. A method of positioning an external charging device relative to an implantable medical device, the method comprising: establishing wireless communication between a processing device and an external charging device, wherein the charging device is configured for transcutaneously charging of an implanted medical device and the processing device having a software application thereon for assessing charging alignment; charging the implantable medical device with the external charging device when at least a first-order alignment is achieved; receiving, with the processing device, one or more charging parameters or an associated charging metric from the external charging device during transcutaneous charging of the implanted medical device via wireless communication; displaying on a display of a user device with the software application, a real-time charging efficiency indicator based on the one or more charging parameters or metric, wherein the charging efficiency indicator corresponds to a fine-tuned alignment between the external charging device and the implanted medical device; and moving the external charging device on the patient in response to variations in the charging efficiency indicator, shown on the display, to determine an optimal position of the external charging device for charging.

21. The method of claim 20, wherein the step of moving the external charging device is carried out by a field technician, a representative, or a clinical care specialist associated with an implantable medical device provider.

22. The method of claim 20, wherein the software application is configured to be used only by authorized users.

23. The method of claim 20, wherein the external charging device is configured to communicate by a first type of communication with the implantable medical device and to communicate by a second type of communication with the processing device.

24. The method of claim 23, wherein the first type of communication is MedRadio and the second type of communication is Bluetooth.

25. The method of claim 22, wherein the external charging device is a charging device configured for use only with the software application.

26. The method of claim 25, further comprising: when the implantable medical device is in a hibernation and/or low battery mode, the external charging device is configured to charge the implantable medical device while operating in an accelerated charging mode as compared with a standard charging mode.

27. The method of claim 26, wherein the external charging device is configured to charge the implantable medical device in the accelerated charging mode when the implantable medical device is in a hibernation and/or a low battery state at least until communication may be established.

28. The method of claim 27, wherein the external charging device is further configured to charge the implantable medical device at a same rate as the standard charging mode after communication is established.

29. The method of claim 20, further comprising: displaying the charging efficiency indicator as a bar that extends between multiple differing charging efficiency levels and that dynamically updates to show a current charging efficiency level in real time.

30. The method of claim 29, further comprising: displaying a peak level of charging efficiency during a charging session on the charging efficiency indicator.

31. The method of claim 30, further displaying one or more additional indicators on the display of the user device, wherein the one or more additional indicators include any of: a charging efficiency history indicator; a battery charge status; a connection status; a charging time indicator; an estimated charging time remaining; a total estimated charging time; and any combination thereof.

32. A system for wireless charging of an implantable medical device, the system comprising: an implantable medical device, having a housing, configured to be implanted within a body of a patient, the implantable medical device including an energy storage device disposed within the housing of the implantable medical device and a receiving coil disposed within the housing and electrically coupled to the energy storage device; an external charging device having a housing, the external charging device including a charging coil disposed within the housing of the external charging device, the charging coil configured to magnetically couple with the receiving coil of the implantable medical device and the receiving coil configured to inductively receive energy from the charging coil and configured to provide at least a portion of the energy from the receiving coil to the energy storage device; and a portable user device, the portable user device configured to wirelessly communicate with at least one of the external charging device and the implantable medical device, the portable user device including a user interface and a processor configured to run a software application configured to aid in optimal positioning of the external charging device relative to the implantable medical device based on a real-time visual indicator, provided on the user interface, of charging efficiency.

*    *    *    *    *